(12) United States Patent
Lucet-Levannier et al.

(10) Patent No.: US 8,535,647 B2
(45) Date of Patent: *Sep. 17, 2013

(54) COSMETIC/SUNSCREEN COMPOSITIONS CONTAINING DIBENZOYLMETHANE COMPOUNDS AND DITHIOLANE COMPOUND PHOTOSTABILIZERS THEREFOR

(75) Inventors: Karine Lucet-Levannier, Reuil-Malmaison (FR); Benoit Muller, Paris (FR)

(73) Assignee: L'Oreal, Paris (FR)

( * ) Notice: Subject to any disclaimer, the term of this patent is extended or adjusted under 35 U.S.C. 154(b) by 569 days.

This patent is subject to a terminal disclaimer.

(21) Appl. No.: 12/588,197

(22) Filed: Oct. 7, 2009

(65) Prior Publication Data

US 2010/0086502 A1   Apr. 8, 2010

Related U.S. Application Data

(60) Provisional application No. 61/107,075, filed on Oct. 21, 2008.

(30) Foreign Application Priority Data

Oct. 8, 2008   (FR) ..................... 08 56810

(51) Int. Cl.
*A61K 8/00*   (2006.01)
*A61K 8/18*   (2006.01)
*A61K 31/385*   (2006.01)
*A61Q 17/04*   (2006.01)
*A01N 43/26*   (2006.01)

(52) U.S. Cl.
USPC ........................................... 424/59; 514/440

(58) Field of Classification Search
USPC ........................................... 514/440
See application file for complete search history.

(56) References Cited

U.S. PATENT DOCUMENTS

| 5,672,337 | A | * | 9/1997 | Ascione et al. | 424/59 |
| 6,013,663 | A |  | 1/2000 | Fujita et al. |  |
| 2010/0135942 | A1 | * | 6/2010 | Marat | 424/62 |
| 2010/0197759 | A1 | * | 8/2010 | Marat et al. | 514/422 |

FOREIGN PATENT DOCUMENTS

| EP | 0717982 B2 | 2/2001 |
| FR | 2908769 B1 | 12/2008 |

OTHER PUBLICATIONS

Fuji et al., "Preparation and formulation of cyclic dithio derivatives as remedies for diabetic kidney diseases, hypoglycemic agents, hypolipidemic agents, and lenitives for digestive disorders", XP 002524712, 1998.

* cited by examiner

*Primary Examiner* — Fereydoun G Sajjadi
*Assistant Examiner* — Michael B Pallay
(74) *Attorney, Agent, or Firm* — Buchanan Ingersoll & Rooney PC

(57) ABSTRACT

Cosmetic/sunscreen compositions contain a combination of at least one dibenzoylmethane sunscreen compound and a photostabilizing amount of at least one dithiolane compound of formula (I) below:

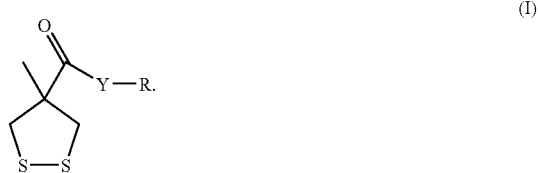

16 Claims, No Drawings

COSMETIC/SUNSCREEN COMPOSITIONS CONTAINING DIBENZOYLMETHANE COMPOUNDS AND DITHIOLANE COMPOUND PHOTOSTABILIZERS THEREFOR

CROSS-REFERENCE TO PRIORITY/PCT APPLICATIONS

This application claims priority under 35 U.S.C. §§119 and 120 of FR 0856810, filed Oct. 8, 2008, and of U.S. Provisional Application No. 61/107,075, filed Oct. 21, 2008, each hereby expressly incorporated by reference and each assigned to the assignee hereof.

BACKGROUND OF THE INVENTION

1. Technical Field of the Invention

The present invention relates to cosmetic/sunscreen compositions containing a combination of at least one screening agent comprising a dibenzoylmethane compound and at least one particular dithiolane compound of formula (I), the definition of which is given hereinbelow.

The invention also relates to a process for radiation-photostabilizing at least one screening agent comprising a dibenzoylmethane compound with an effective amount of at least one particular dithiolane compound of formula (I).

The present invention also relates to the formulation of at least one particular dithiolane compound of formula (I) in a composition comprising, in a cosmetically acceptable support, at least one dibenzoylmethane compound, for the purpose of improving the efficacy of the said composition with respect to the screening of UV-A rays.

2. Description of Background and/or Related and/or Prior Art

It is known that light radiation with wavelengths of from 280 nm to 400 nm permits tanning of the human epidermis and that light rays with wavelengths more particularly from 280 to 320 nm, known as UV-B rays, cause skin burns and erythema which can harm the development of a natural tan. For these reasons, as well as for aesthetic reasons, there is a constant demand for means of controlling this natural tanning in order thus to control the color of the skin; this UV-B radiation should thus be screened from the skin.

It is also known that UV-A rays, with wavelengths from 320 to 400 nm, which cause tanning of the skin, are liable to induce adverse changes therein, in particular in the case of sensitive skin or skin that is continually exposed to solar radiation. UV-A rays cause in particular a loss of elasticity of the skin and the appearance of wrinkles leading to premature aging of the skin. They promote triggering of the erythemal reaction or amplify this reaction in certain individuals and may even be the cause of phototoxic or photoallergic reactions. Thus, for aesthetic and cosmetic reasons, for instance conservation of the skin's natural elasticity, an increasingly large number of individuals wish to control the effect of UV-A rays on their skin. It is thus desirable also to screen out UV-A radiation.

For the purpose of protecting the skin and keratin materials against UV radiation, anti-sun/sunscreen compositions comprising organic screening agents that are active in the UV-A range and in the UV-B range are generally used. The majority of these screening agents are liposoluble.

In this respect, one particularly advantageous family of UV-A screening agents currently consists of dibenzoylmethane compounds, and in particular 4-tert-butyl-4'-methoxydibenzoylmethane, which have high intrinsic absorbing power. These dibenzoylmethane compounds, which are products that are now well known per se as screening agents that are active in the UV-A range, are described in particular in FR-A-2,326,405 and FR-A-2,440,933, and also in EP-A-0, 114,607; 4-tert-butyl-4'-methoxydibenzoylmethane is moreover currently marketed under the trademark Parsol 1789® by DSM Nutritional Products.

Unfortunately, it has been found that dibenzoylmethane compounds are products that are relatively sensitive to ultraviolet radiation (especially UV-A), i.e., more specifically, they have an annoying tendency to be degraded more or less quickly under the action of this UV. Thus, this substantial lack of photochemical stability of dibenzoylmethane compounds towards ultraviolet radiation, to which they are by nature intended to be subjected, does not make it possible to ensure constant protection during prolonged exposure to the sun, and so the user must make repeated applications at regular and close time intervals to obtain effective protection of the skin against UV rays.

Photostabilization of dibenzoylmethane compounds towards UV-radiation with amide compounds thus constitutes, at the present time, a problem that has still not been solved entirely satisfactorily.

SUMMARY OF THE INVENTION

It has now surprisingly been discovered that by combining the dibenzoylmethane compounds mentioned above with particular dithiolane compounds of formula (I) that will be defined later in detail, it is possible to substantially and appreciably further improve the photochemical stability (or photostability) of these same dibenzoylmethane compounds and their efficacy in the UV-A range. Compositions containing such a combination also give on application more uniform distribution of the dibenzoylmethane screening agent.

This discovery forms the basis of the present invention.

Thus, in accordance with one of the aspects of the present invention, compositions are now provided comprising, formulated into a cosmetically acceptable support, at least one UV-screening system, which comprises:

a) at least one dibenzoylmethane compound, and b) at least one dithiolane compound of formula (I), the definition of which is given hereinbelow.

This invention also features a process for improving the chemical stability towards UV radiation of at least one dibenzoylmethane compound, which entails combining the said at least one dibenzoylmethane compound with an effective amount of at least one dithiolane compound of formula (I).

The present invention also features the formulation of at least one dithiolane compound of formula (I), in a composition comprising, in a cosmetically acceptable support, at least one dibenzoylmethane compound, for the purpose of improving the efficacy of the said composition with respect to UV-A rays.

Other characteristics, aspects and advantages of the invention will become apparent from the detailed description that follows.

The term "cosmetically acceptable" means compatible with the skin and/or its integuments, which has a pleasant color, odor and feel, and which does not cause any unacceptable discomfort (stinging, tautness or redness) liable to put the consumer off using this composition.

The term "effective amount" means an amount that is sufficient to obtain an appreciable and significant improvement in the photostability of the dibenzoylmethane derivative(s) in the cosmetic composition. This minimum amount of dithiolane compound of formula (I), which may vary according to the nature of the support adopted for the composition, may be determined without any difficulty by means of a standard test for measuring photostability, such as that given in the examples hereinbelow.

DETAILED DESCRIPTION OF BEST MODE AND SPECIFIC/PREFERRED EMBODIMENTS OF THE INVENTION

The dithiolane compounds in accordance with the present invention correspond to formula (I) below:

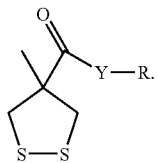
(I)

in which:

Y is O or $NR_1$;

$R_1$ is a hydrogen atom, a saturated linear $C_1$-$C_{20}$ or branched $C_3$-$C_{20}$ or unsaturated $C_2$-$C_{20}$ alkyl hydrocarbon-based radical, an aryl radical optionally substituted with one or more hydroxyl groups and/or with one or more $C_1$-$C_8$ alkoxy radicals;

R is a hydrogen atom, a saturated linear $C_1$-$C_{20}$ or branched $C_3$-$C_{20}$ or unsaturated $C_2$-$C_{20}$ alkyl hydrocarbon-based radical, an aryl radical or a saturated $C_1$-$C_8$ alkyl radical containing an aryl substituent optionally substituted with one or more hydroxyl groups and/or with one or more $C_1$-$C_8$ alkoxy radicals;

R optionally bears one or more substituents selected from among $OR_2$, $SR_2$, $NR_2R_3$ and $COOR_2$ in which:

$R_2$ is a hydrogen atom or a saturated linear $C_{1-5}$ or branched $C_{3-5}$ or unsaturated $C_{2-5}$ hydrocarbon-based radical, or an aryl radical;

$R_3$ is a hydrogen atom, a saturated linear $C_{1-5}$ or branched $C_{3-5}$ or unsaturated $C_{2-5}$ hydrocarbon-based radical, an aryl radical, or an acetyl radical;

R and $R_1$ may together form a ring member selected from among pyrrolidine, pyrroline, piperidine, piperazine, morpholine, thiomorpholine and azepine; and also the salts, chelates, solvates and optical isomers thereof.

The salts of the compounds of the present invention include conventional non-toxic salts of the said compounds, such as those formed from organic or mineral acids. Examples thereof include the salts of mineral acids, such as sulfuric acid, hydrochloric acid, hydrobromic acid, hydriodic acid, phosphoric acid or boric acid. Also exemplary are the salts of organic acids, which may include one or more carboxylic, sulfonic or phosphonic acid groups. They may be linear, branched or cyclic aliphatic acids, or, alternatively, aromatic acids. These acids may also include one or more heteroatoms selected from among O and N, for example in the form of hydroxyl groups. Especially exemplary are propionic acid, acetic acid, terephthalic acid, citric acid and tartaric acid. The salts of organic or mineral bases such as the triethanolamine, aminopropanediol, sodium or zinc salts.

The solvates that are acceptable for the non-therapeutic use of the compounds described in the present invention include conventional solvates such as those formed during the final step of preparation of the said compounds due to the presence of solvents. Examples include solvates due to the presence of water or of linear or branched alcohols such as ethanol or isopropanol.

The optical isomers are, especially, enantiomers and diastereoisomers.

Preferentially, the aryl radicals denote phenyl or benzyl.

Preferentially, the alkoxy radicals are linear $C_1$-$C_4$ radicals and more preferentially methoxy, ethoxy, propoxy or butoxy and even more preferentially methoxy.

Preferentially, the hydrocarbon-based radicals are linear or branched alkyls and may be selected from among: methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl.

More preferentially, the hydrocarbon-based radicals are saturated linear or branched $C_1$-$C_8$ alkyl radicals: methyl, ethyl, propyl, isopropyl, butyl, isobutyl, tert-butyl, pentyl, hexyl, heptyl, octyl.

Even more preferentially, when Y is $NR_1$, then $R_1$=H.

Most preferentially, R=H or a $C_1$-$C_8$ alkyl radical.

Among the compounds of formula (I), more particularly exemplary are the following:

| No. | Structure | Chemical name |
|---|---|---|
| 1. | ![structure with CO2H] | 4-Methyl-1,2-dithiolane-4-carboxylic acid |
| 2 | ![structure with O, NH2] | 4-Methyl-1,2-dithiolane-4-carboxamide |

-continued

| No. | Structure | Chemical name |
|---|---|---|
| 3. | 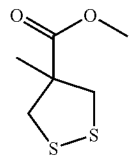 | Méthyl 4-methyl-1,2-dithiolane-4-carboxylate |
| 4. | 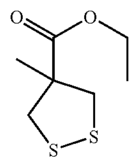 | Ethyl 4-methyl-1,2-dithiolane-4-carboxylate |
| 5. | 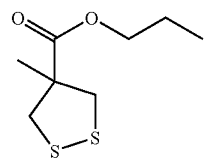 | Propyl 4-methyl-1,2-dithiolane-4-carboxylate |
| 6. | 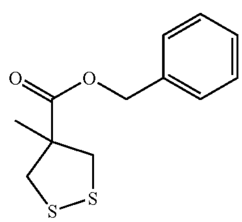 [SMILES: CC1(C(=O)OCc2ccccc2)CSSC1] | Benzyl 4-methyl-1,2-dithiolane-4-carboxylate |
| 7. | 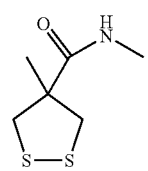 | N-Methyl 4-methyl-1,2-diothiolane-4-carboxamide |
| 8. | 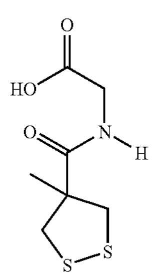 | {[(4-Methyl-1,2-dithiolan-4-yl)carbonyl]amino}acetic acid |
| 9. | 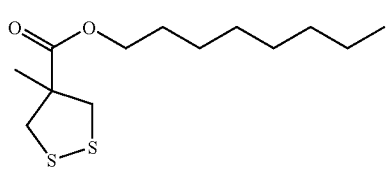 [SMILES: CCCCCCCCOC(=O)C1(C)CSSC1] | Octyl 4-methyl-1,2-dithiolane-4-carboxylate |
| 10. | 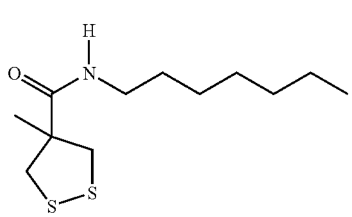 [SMILES: CCCCCCCNC(=O)C1(C)CSSC1] | N-Heptyl-4-methyl-1,2-dithiolane-4-carboxamide |

-continued

| No. | Structure | Chemical name |
|---|---|---|
| 11. | 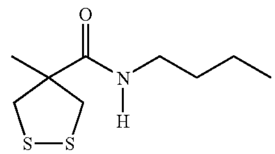 | N-Butyl-4-methyl-1,2-dithiolane-4-carboxamide |
| 12. | 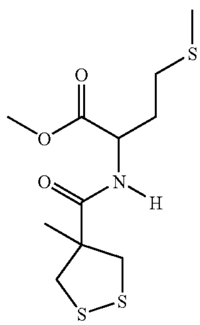 | Methyl 2-{[(4-methyl-1,2-dithiolan-4-yl)carbonyl]amino}-4-(methylsulfanyl)butanoate |
| 13. | 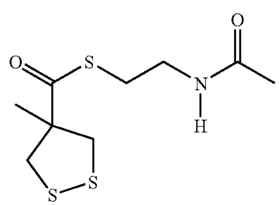 | S-[2-(Acetylamino)ethyl] 4-methyl-1,2-dithiolane-4-carbothioate |
| 14. | 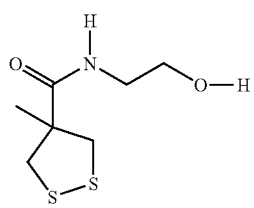 | N-(2-Hydroxyethyl)-4-methyl-1,2-dithiolane-4-carboxamide |
| 15. | 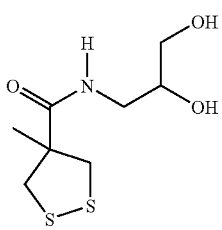 | N-(2,3-Dihydroxypropyl)-4-methyl-1,2-dithiolane-4-carboxamide |
| 16. | 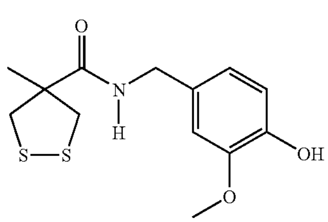 [SMILES: COc1cc(CNC(=O)C2(C)CSSC2)ccc1O] | N-(4-Hydroxy-3-methoxybenzyl)-4-methyl-1,2-dithiolane-4-carboxamide |
| 17. | 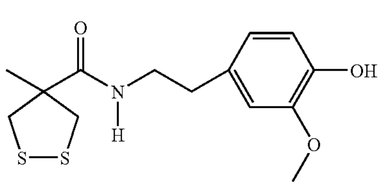 [SMILES: COc1cc(CCNC(=O)C2(C)CSSC2)ccc1O] | N-[2-(4-Hydroxy-3-methoxyphenyl)ethyl]-4-methyl-1,2-dithiolane-4-carboxamide |

-continued

| No. | Structure | Chemical name |
|---|---|---|
| 18. | 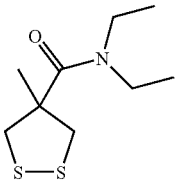 | N,N-Diethyl-4-methyl-1,2-dithiolane-4-carboxamide |
| 19. | 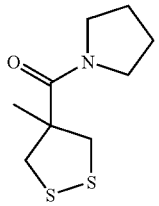 | [(4-Methyl-1,2-dithiolan-4-yl)carbonyl]pyrrolidine |
| 20. | 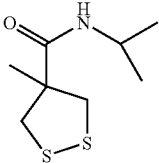 | 4-Methyl-N-(1-methylethyl)-1,2-dithiolane-4-carboxamide |
| 21. | 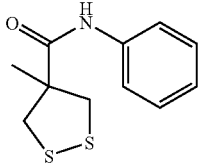 | 4-Methyl-N-phenyl-1,2-dithiolane-4-carboxamide |
| 22. | 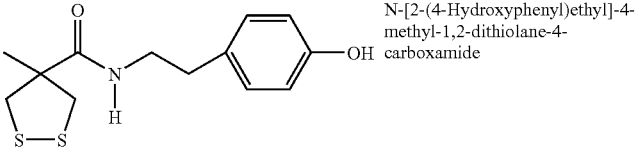 | N-[2-(4-Hydroxyphenyl)ethyl]-4-methyl-1,2-dithiolane-4-carboxamide |
| 23. | 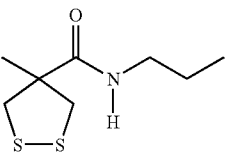 | N-Propyl-4-methyl-1,2-dithiolane-4-carboxamide |
| 24. | 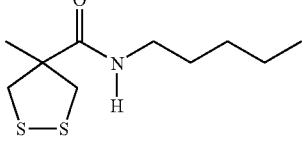 | N-Pentyl-4-methyl-1,2-dithiolane-4-carboxamide |
| 25. | 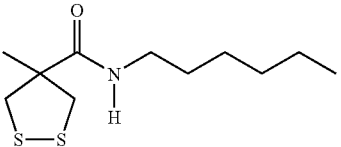 | N-Hexyl-4-methyl-1,2-dithiolane-4-carboxamide |

Among these compounds, the following compounds are more particularly preferred:

| No. | Structure | Chemical name |
|---|---|---|
| 1. | 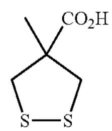 | 4-Methyl-1,2-dithiolane-4-carboxylic acid |
| 2. | 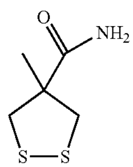 | 4-Methyl-1,2-dithiolane-4-carboxamide |
| 9. | 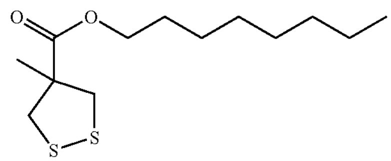 [SMILES: CCCCCCCCOC(=O)C1(C)CSSC1] | Octyl 4-methyl-1,2-dithiolane-4-carboxylate |
| 10. | 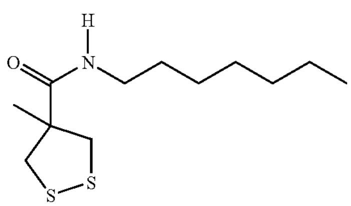 [SMILES: CCCCCCCNC(=O)C1(C)CSSC1] | N-Heptyl-4-methyl-1,2-dithiolane-4-carboxamide |

Synthesis:

The compounds of formula (I) may be prepared according to the routes described below and documented in the review by Lene Teuber, Sulfur reports, 9(4), 257-349, 1990: *Naturally occurring 1,2-dithiolanes and 1,2,3-trithianes. Chemical and biological properties*, and in EP-0,869,126 A1.

Starting with 2,2-bis(hydroxymethyl)propionic acid (CAS:4767-03-7), via functionalization of the hydroxyls into leaving groups X *(alkyl or aryl sulfonates such as mesylates or tosylates or halogens such as iodine, bromine or chlorine) followed by introduction of sulfur according to the following reaction scheme:*

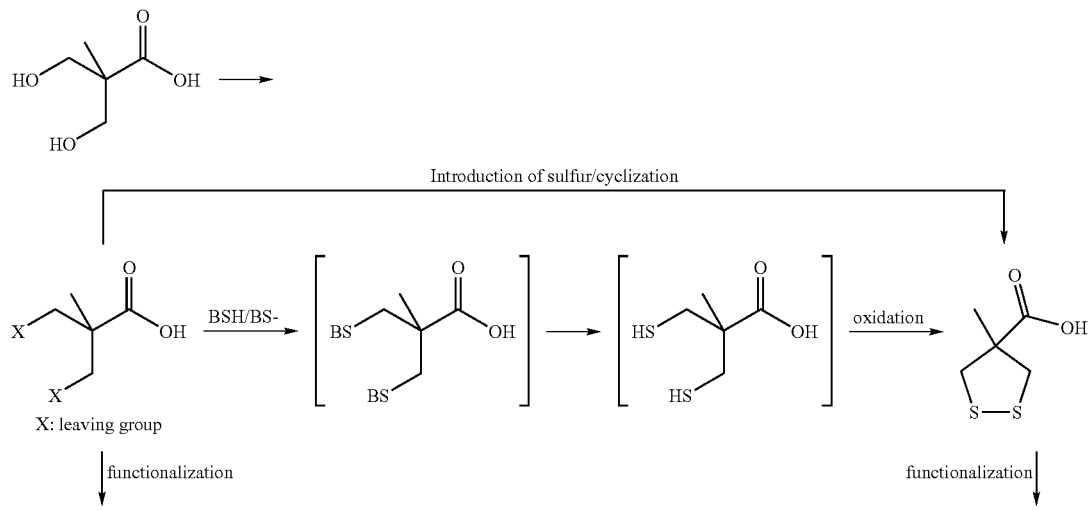

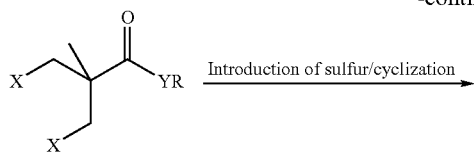 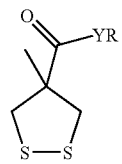

This introduction of sulfur may be performed:
(i) in one step using a metal disulfide (such as $Na_2S_2$) or tetrathiomolybdate salts in polar protic or aprotic solvents (for example water, DMF, methanol or acetonitrile) to give the dithiolane;
(ii) or in two steps by forming a dithiol intermediate, which, in the presence of an oxidizing agent (oxygen, DMSO, $FeCl_3$, $I_2$, $Br_2$, sodium iodide, thallium trifluoroacetates, silver triflates, hydrogen peroxide, sodium iodate or periodate, sodium hypochlorite, potassium ferricyanide or chromium oxide), in neutral or basic medium, leads to the formation of the dithiolane. In this case, the dithiol is obtained by transformation (in basic or acidic medium) in a polar or apolar solvent of an intermediate species via thioacetic acid $CH_3COSH$ derivatives (in the presence of base), with thiourea or NaSH, via the formation of dithiosulfonates (Bunte salts).

Functionalization of the carboxylic acid COOH into a function COYR may be performed according to the standard acid activation methods (described in Comprehensive Organic Transformations by R. Larock, Wiley VCH Ed. in the chapter: Interconversion of nitriles, carboxylic acids and derivatives). Preferably, the methods used favor proceeding via the acid chloride (by using thionyl or oxalyl chloride, or 1-chloro-N,N,2-trimethyl-1-propenamine) or via the formation of a mixed anhydride (using alkyl chloroformates) or the use of carbodiimides or diethyl cyanophosphate (Phosphorus in organic synthesis—XI, Amino acids and peptides—XXI, *Reaction of diethyl phosphorocyanidate with carboxylic acids. A new synthesis of carboxylic esters and amides*, Tetrahedron, 32, 1976, 2211-2217).*

The solvents used may be polar or apolar, and protic or aprotic (for example toluene, dichloromethane, THF, DMF, acetonitrile, water, methanol or isopropanol).

All these reactions may be performed at temperatures of from –20° C. to 100° C.

Advantageously, compound 1 may be obtained according to the route described below, starting with dichloropivalic acid according to a one-pot process, terminating with a precipitation.

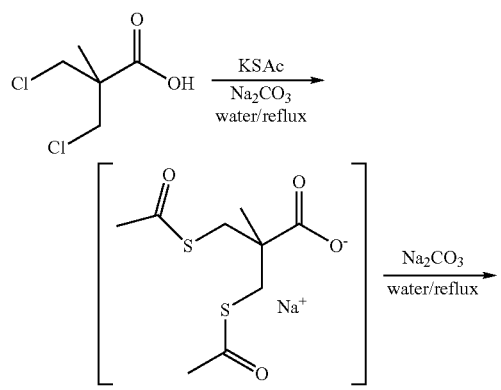

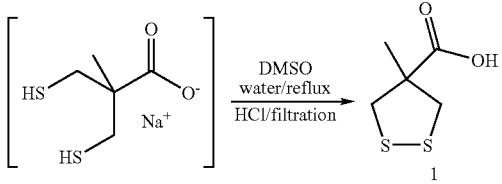

Advantageously, compound 2 may be obtained from compound 1, preferentially using isobutyl chloroformate or oxalyl chloride.

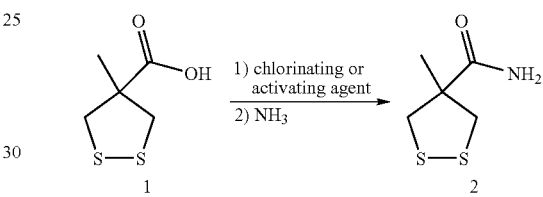

The dithiolane compounds of formula (I) are preferably present in the compositions according to the invention in a content ranging from 0.1% to 40% by weight and preferably ranging from 0.1% to 30% by weight relative to the total weight of the composition.

The dibenzoylmethane compounds that are especially exemplary are:
2-methyldibenzoylmethane
4-methyldibenzoylmethane
4-isopropyldibenzoylmethane
4-tert-butyldibenzoylmethane
2,4-dimethyldibenzoylmethane
2,5-dimethyldibenzoylmethane
4,4'-diisopropyldibenzoylmethane
4,4'-dimethoxydibenzoylmethane
4-tert-butyl-4'-methoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl-4-tert-butyl-4'-methoxydibenzoylmethane.

Among the dibenzoylmethane derivatives mentioned above, 4-isopropyldibenzoylmethane will be used in particular, which is marketed under the trademark Eusolex 8020 by Merck, and corresponds to the following formula:

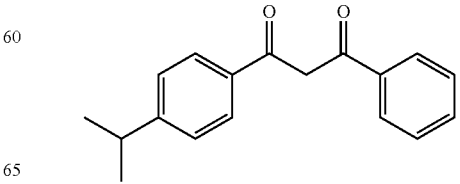

It is most particularly preferred to use 4-(tert-butyl)-4'-methoxydibenzoylmethane or Butyl Methoxy Dibenzoylmethane, marketed under the trademark Parsol 1789 by DSM Nutritional Products; this screening agent corresponds to the following formula:

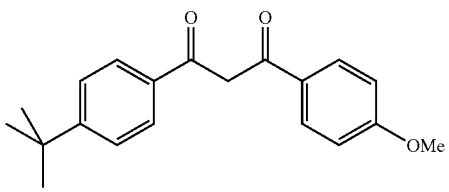 [SMILES: COc1ccc(C(=O)CC(=O)c2ccc(C(C)(C)C)cc2)cc1]

The dibenzoylmethane compound (s) may be present in the compositions in accordance with the invention in contents preferably ranging from 0.01% to 10% by weight and more preferably from 0.1% to 6% by weight relative to the total weight of the composition.

The compositions in accordance with the invention may also comprise other additional UV-A-active and/or UV-B-active organic or mineral UV-screening agents that are water-soluble or liposoluble or even insoluble in the cosmetic solvents commonly employed.

Needless to say, one skilled in this art will take care to select the optional additional screening agent(s) and/or the amounts thereof such that the advantageous properties intrinsically associated with the compositions in accordance with the invention are not, or are not substantially, adversely affected by the envisaged addition(s), especially the improvement in the photostability of the dibenzoylmethane derivative.

The additional organic screening agents are selected especially from among anthranilates; cinnamic derivatives; salicylic derivatives; camphor derivatives; benzophenone derivatives; $\beta,\beta$-diphenylacrylate derivatives; triazine derivatives; benzotriazole derivatives; benzalmalonate derivatives, especially those indicated in U.S. Pat. No. 5,624,663; benzimidazole derivatives; imidazolines; bis-benzazolyl derivatives as described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2,303,549, DE-197,26,184 and EP-893,119; benzoxazole derivatives as described in EP-0,832,642, EP-1,027,883, EP-1,300,137 and DE-101,62,844; screening polymers and screening silicones such as those described especially in WO 93/04665; α-alkylstyrene-based dimers, such as those described in DE-198,55,649; 4,4-diarylbutadienes such as those described in EP-0,967,200, DE-197,46,654, DE-197,55,649, EP-A-1,008,586, EP-1-133,980 and EP-133,981; merocyanin derivatives such as those described in WO 04/006 878, WO 05/058 269 and WO 06/032 741; and mixtures thereof.

Examples of additional organic photoprotective agents include those indicated hereinbelow under their INCI name:

Cinnamic Derivatives:
Ethylhexyl methoxycinnamate marketed in particular under the trademark Parsol MCX by DSM Nutritional Products, Inc.,
Isopropyl methoxycinnamate,
Isoamyl methoxycinnamate marketed under the trademark Neo Heliopan E 1000 by Symrise,
Cinoxate,
DEA methoxycinnamate,
Diisopropyl methylcinnamate,
Glyceryl ethylhexanoate dimethoxycinnamate.

para-Aminobenzoic Acid Derivatives:
PABA,
Ethyl PABA,
Ethyl dihydroxypropyl PABA,
Ethylhexyl dimethyl PABA marketed in particular under the trademark Escalol 507 by ISP,
Glyceryl PABA,
PEG-25 PABA marketed under the trademark Uvinul P25 by BASF.

Salicylic Derivatives:
Homosalate marketed under the trademark Eusolex HMS by Rona/EM Industries,
Ethylhexyl salicylate marketed under the trademark Neo Heliopan OS by Symrise,
Dipropylene glycol salicylate marketed under the trademark Dipsal by Scher,
TEA salicylate marketed under the trademark Neo Heliopan TS by Symrise.

$\beta,\beta$-Diphenylacrylate derivatives:
Octocrylene marketed in particular under the trademark Uvinul N539 by BASF,
Etocrylene marketed in particular under the trademark Uvinul N35 by BASF.

Benzophenone Derivatives:
Benzophenone-1 marketed under the trademark Uvinul 400 by BASF,
Benzophenone-2 marketed under the trademark Uvinul D50 by BASF,
Benzophenone-3 or Oxybenzone marketed under the trademark Uvinul M40 by BASF,
Benzophenone-4 marketed under the trademark Uvinul MS40 by BASF,
Benzophenone-5,
Benzophenone-6 marketed under the trademark Helisorb 11 by Norquay,
Benzophenone-8 marketed under the trademark SpectraSorb UV-24 by American Cyanamid,
Benzophenone-9 marketed under the trademark Uvinul DS-49 by BASF,
Benzophenone-12
n-hexyl 2-(4-diethylamino-2-hydroxybenzoyl)benzoate marketed under the trademark Uvinul A+ by BASF.

Benzylidenecamphor Derivatives:
3-Benzylidenecamphor manufactured under the trademark Mexoryl SD by Chimex,
4-Methylbenzylidenecamphor marketed under the trademark Eusolex 6300 by Merck,
Benzylidenecamphorsulfonic acid manufactured under the trademark Mexoryl SL by Chimex,
Camphor benzalkonium methosulfate manufactured under the trademark Mexoryl SO by Chimex,
Terephthalylidenedicamphorsulfonic acid manufactured under the trademark Mexoryl SX by Chimex,
Polyacrylamidomethylbenzylidenecamphor manufactured under the trademark Mexoryl SW by Chimex.

Phenylbenzimidazole Derivatives:
Phenylbenzimidazolesulfonic acid marketed in particular under the trademark Eusolex 232 by Merck,
Disodium phenyl dibenzimidazole tetrasulfonate marketed under the trademark Neo Heliopan AP by Symrise.

Phenylbenzotriazole Derivatives:
Drometrizole trisiloxane marketed under the trademark Silatrizole by Rhodia Chimie,
Methylenebis(benzotriazolyl)tetramethylbutylphenol marketed in solid form under the trademark MIXXIM BB/100 by Fairmount Chemical, or in micronized form as an aqueous dispersion under the trademark Tinosorb M by Ciba Specialty Chemicals.

Triazine Derivatives:

Bis(ethylhexyloxyphenol)methoxyphenyltriazine marketed under the trademark Tinosorb S by Ciba Geigy, Ethylhexyltriazone marketed in particular under the trademark Uvinul T150 by BASF, Diethylhexylbutamidotriazone marketed under the trademark Uvasorb HEB by Sigma 3V, 2,4-bis(n-butyl 4'-aminobenzoate)-6-(aminopropyltrisiloxane)-s-triazine, 2,4,6-tris(dineopentyl 4'-aminobenzalmalonate)-s-triazine 2,4,6-tris(diisobutyl 4'-aminobenzalmalonate)-s-triazine, 1a 2,4bis(4'-aminobenzoate de n-butyle)-6-(aminopropyltrisiloxane)-s-triazine, 2,4-bis(dineopentyl 4'-aminobenzalmalonate)-6-(n-butyl 4'-aminobenzoate)-s-triazine, the symmetrical triazine screening agents described in U.S. Pat. No. 6,225,467, WO 2004/085 412 (see compounds 6 and 9) or the document Symmetrical Triazine Derivatives IP.COM Journal, IP.COM INC West Henrietta, N.Y., US (20 Sep. 2004), especially 2,4,6-tris(biphenyl)-1,3,5-triazines (in particular 2,4,6-tris(biphenyl-4-yl-1,3,5-triazine) and 2,4,6-tris(terphenyl)-1,3,5-triazine which is also mentioned in WO 06/035 000, WO 06/034 982, WO 06/034 991, WO 06/035 007, WO 2006/034 992 and WO 2006/034 985.

Anthranilic Derivatives:

Menthyl anthranilate marketed under the trademark Neo Heliopan MA by Symrise.

Imidazoline Derivatives:

Ethylhexyldimethoxybenzylidenedioxoimidazoline propionate.

Benzalmalonate Derivatives:

Polyorganosiloxane containing benzalmalonate functions, for instance Polysilicone-15, marketed under the trademark Parsol SLX by DSM Nutritional products, Inc.

4,4-Diarylbutadiene Derivatives:

1,1-Dicarboxy(2,2'-dimethylpropyl)-4,4-diphenylbutadiene.

Benzoxazole Derivatives:

2,4-bis[5-(1-dimethylpropyl)benzoxazol-2-yl(4-phenyl)imino]-6-(2-ethylhexyl)imino-1,3,5-triazine marketed under the trademark Uvasorb K2A by Sigma 3V.

Merocyanin Derivatives:

Octyl 5-N,N-diethylamino-2-phenylsulfonyl-2,4-pentadienoate, and mixtures thereof.

The preferred organic photoprotective agents are selected from among:

Ethylhexyl methoxycinnamate,
Ethylhexyl salicylate,
Homosalate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Bis(ethylhexyloxyphenol)methoxyphenyltriazine,
Ethylhexyltriazone,
Diethylhexylbutamidotriazone,
2,4-bis(4'-aminobenzoate of n-butyl)-6-(aminopropyltrisiloxane)-s-triazine,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4,6-Tris(biphenyl-4-yl)-1,3,5-triazine,
2,4,6-Tris(terphenyl)-1,3,5-triazine,
Drometrizole trisiloxane,
Polysilicone-15,
1,1-Dicarboxy(2,2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine,
Octyl 5-N,N-diethylamino-2-phenylsulfonyl-2,4-pentadienoate, and mixtures thereof.

The additional mineral screening agents are selected from among coated or uncoated metal oxide pigments in which the mean size of the primary particles is preferentially from 5 nm to 100 nm (preferably from 10 nm to 50 nm), for instance titanium oxide (amorphous or crystallized in rutile and/or anatase form), iron oxide, zinc oxide, zirconium oxide or cerium oxide pigments, which are all UV-photoprotective agents that are well known per se.

The pigments may be coated or uncoated.

The coated pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminum salts of fatty acids, metal alkoxides (of titanium or of aluminum), polyethylene, silicones, proteins (collagen, elastin), alkanolamines, silicon oxides, metal oxides or sodium hexametaphosphate.

As is known, silicones are organosilicon polymers or oligomers of linear or cyclic, branched or crosslinked structure, of variable molecular weight, obtained by polymerization and/or polycondensation of suitably functionalized silanes, and consist essentially of a repetition of main units in which the silicon atoms are linked together via oxygen atoms (siloxane bond), optionally substituted hydrocarbon-based radicals being directly attached via a carbon atom to the said silicon atoms.

The term "silicones" also includes the silanes required for their preparation, in particular alkyl silanes.

The silicones used for coating the nanopigments that are suitable for the present invention are preferably selected from among the group containing alkyl silanes, polydialkylsiloxanes and polyalkylhydrogenosiloxanes. Even more preferentially, the silicones are selected from among the group containing octyltrimethylsilane, polydimethylsiloxanes and polymethylhydrogenosiloxanes.

Needless to say, before being treated with silicones, the metal oxide pigments may have been treated with other surface agents, in particular with cerium oxide, alumina, silica, aluminum compounds or silicon compounds, or mixtures thereof.

The coated pigments are more particularly titanium oxides that have been coated:

with silica, such as the product Sunveil from the company Ikeda and the product Eusolex T-AVO from the company Merck, with silica and iron oxide, such as the product Sunveil F from the company Ikeda, with silica and alumina, such as the products Microtitanium Dioxide MT 500 SA and Microtitanium Dioxide MT 100 SA from the company Tayca, Tioveil from the company Tioxide and Mirasun TiW 60 from the company Rhodia, with alumina, such as the products Tipaque TTO-55 (B) and Tipaque TTO-55 (A) from the company Ishihara and UVT 14/4 from the company Kemira, with alumina and aluminum stearate, such as the product Microtitanium Dioxide MT 100 TV, MT 100 TX, MT 100 Z and MT-01 from the company Tayca, and the products Solaveil CT-10 W, Solaveil CT 100 and Solaveil CT 200 from the company Uniqema, with silica, alumina and alginic acid, such as the product MT-100 AQ from the company Tayca, with alumina and aluminum laurate, such as the product Microtitanium Dioxide MT 100 S from the company Tayca, with iron oxide and iron stearate, such as the product Microtitanium Dioxide MT 100 F from the company Tayca, with zinc oxide and zinc stearate, such as the product BR351 from the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminum stearate and treated with a silicone, such as the product STT-30-DS from the company Titan Kogyo, with silica and treated with a silicone, such as the product UV-Titan X 195 from the company Kemira, or the product SMT-100 WRS from the company Tayca, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca.

Other titanium oxide pigments treated with a silicone are preferably $TiO_2$ treated with octyltrimethylsilane and for which the mean size of the elementary particles ranges from 25 to 40 nm, such as the product marketed under the trademark T 805 by Degussa Silices, $TiO_2$ treated with a polydimethylsiloxane and for which the mean size of the elementary particles is 21 nm, such as the product marketed under the trademark 70250 Cardre UF TiO2SI3 by Cardre, anatase/rutile $TiO_2$ treated with a polydimethylhydrogenosiloxane and for which the mean size of the elementary particles is 25 nm, such as the product marketed under the trademark Microtitanium Dioxide USP Grade Hydrophobic by Color Techniques.

The uncoated titanium oxide pigments are marketed, for example, by Tayca under the trademarks Microtitanium Dioxide MT 500 B or Microtitanium Dioxide MT 600 B, by Degussa under the trademark P 25, by Wacker under the trademark Transparent titanium oxide PW, by Miyoshi Kasei under the trademark UFTR, by Tomen under the trademark ITS and by Tioxide under the trademark Tioveil AQ.

The uncoated zinc oxide pigments are, for example:
those marketed under the trademark Z-Cote by Sunsmart;
those marketed under the trademark Nanox by Elementis;
those marketed under the trademark Nanogard WCD 2025 by Nanophase Technologies.

The coated zinc oxide pigments are, for example:
those marketed under the trademark Z-Cote HP1 by Sunsmart (dimethicone-coated ZnO);
those marketed under the trademark Zinc Oxide CS-5 by Toshibi (ZnO coated with polymethylhydrogenosiloxane);

those marketed under the trademark Nanogard Zinc Oxide FN by Nanophase Technologies (as a 40% dispersion in Finsolv TN, $C_{12}$-$C_{15}$ alkyl benzoate);

those marketed under the trademark Daitopersion ZN-30 and Daitopersion ZN-50 by Daito (dispersions in cyclopolymethylsiloxane/oxyethylenated polydimethylsiloxane, containing 30% or 50% of nanozinc oxides coated with silica and polymethylhydrogenosiloxane);

those marketed under the trademark NFD Ultrafine ZnO by Daikin (ZnO coated with perfluoroalkyl phosphate and copolymer based on perfluoroalkylethyl as a dispersion in cyclopentasiloxane);

those marketed under the trademark SPD-Z1 by Shin-Etsu (ZnO coated with silicone-grafted acrylic polymer, dispersed in cyclodimethylsiloxane);

those marketed under the trademark Escalol Z100 by ISP (alumina-treated ZnO dispersed in an ethylhexyl methoxycinnamate/PVP-hexadecene/methicone copolymer mixture);

those marketed under the trademark Fuji ZnO-SMS-10 by Fuji Pigment (ZnO coated with silica and polymethylsilsesquioxane);

those marketed under the trademark Nanox Gel TN by Elementis (ZnO dispersed at a concentration of 55% in $C_{12}$-$C_{15}$ alkyl benzoate with hydroxystearic acid polycondensate).

The uncoated cerium oxide pigments are marketed under the trademark Colloidal Cerium Oxide by Rhone-Poulenc.

The uncoated iron oxide nanopigments are marketed, for example, by Arnaud under the trademarks Nanogard WCD 2002 (FE 45B), Nanogard Iron FE 45 BL AQ, Nanogard FE 45R AQ and Nanogard WCD 2006 (FE 45R) or by Mitsubishi under the trademark TY-220, The coated iron oxide pigments are marketed, for example, by Arnaud under the trademarks Nanogard WCD 2008 (FE 45B FN), Nanogard WCD 2009 (FE 45B 556), Nanogard FE 45 BL 345 and Nanogard FE 45 BL or by BASF under the trademark Transparent Iron Oxide.

Also exemplary are mixtures of metal oxides, especially of titanium dioxide and of cerium dioxide, including the silica-coated equal-weight mixture of titanium dioxide and of cerium dioxide, marketed by Ikeda under the trademark Sunveil A, and also the alumina, silica and silicone-coated mixture of titanium dioxide and of zinc dioxide, such as the product M 261 marketed by Kemira, or the alumina, silica and glycerol-coated mixture of titanium dioxide and of zinc dioxide, such as the product M 211 marketed by Kemira.

The additional UV-screening agents are generally present in the compositions according to the invention in proportions ranging from 0.01% to 20% by weight relative to the total weight of the composition, and preferably ranging from 0.1% to 10% by weight relative to the total weight of the composition.

The aqueous compositions in accordance with the present invention may also comprise standard cosmetic adjuvants selected especially from fatty substances, organic solvents, ionic or nonionic, hydrophilic or lipophilic thickeners, softeners, humectants, opacifiers, stabilizers, emollients, silicones, anti-foams, fragrances, preservatives, anionic, cationic, nonionic, zwitterionic or amphoteric surfactants, active agents, fillers, polymers, propellants, acidifying or basifying agents or any other ingredient usually used in cosmetics and/or dermatology.

The fatty substances may consist of an oil or a wax other than the apolar waxes as defined above, or mixtures thereof. The term oil means a compound that is liquid at room temperature. The term wax means a compound that is solid or substantially solid at room temperature and whose melting point is generally greater than 35° C.

Oils that are exemplary include mineral oils (paraffin); plant oils (sweet almond oil, *macadamia* oil, grape seed oil or jojoba oil); synthetic oils, for instance perhydrosqualene, fatty alcohols, fatty amides (for instance isopropyl lauroyl sarcosinate marketed under the trademark Eldew SL-205 by Ajinomoto), fatty acids or fatty esters, for instance the $C_{12}$-$C_{15}$ alkyl benzoate marketed under the trademark Finsolv TN or Witconol TN by Witco, 2-ethylphenyl benzoate, for instance the commercial product marketed under the trademark X-Tend 226® by ISP, octyl palmitate, isopropyl lanolate and triglycerides, including capric/caprylic acid triglycerides, and dicaprylyl carbonate marketed under the trademark Cetiol CC by Cognis, oxyethylenated or oxypropylenated fatty esters and ethers; silicone oils (cyclomethicone and polydimethylsiloxanes, or PDMS) or fluoro oils, polyalkylenes, and trialkyl trimellitates such as tridecyl trimellitate.

Waxy compounds that are exemplary include carnauba wax, beeswax, hydrogenated castor oil, polyethylene waxes and polymethylene waxes, for instance the product marketed under the trademark Cirebelle 303 by Sasol.

Among the organic solvents that are exemplary are lower alcohols and polyols. These polyols may be selected from among glycols and glycol ethers, for instance ethylene glycol, propylene glycol, butylene glycol, dipropylene glycol or diethylene glycol.

Hydrophilic thickeners that are exemplary include carboxyvinyl polymers such as the Carbopol products (carbomers) and the Pemulen products (acrylate/$C_{10}$-$C_{30}$-alkylacrylate copolymer); polyacrylamides, for instance the crosslinked copolymers marketed under the trademarks Sepigel 305 (CTFA name: polyacrylamide/$C_{13-14}$ isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulfonic acid polymers and copolymers, which are optionally crosslinked and/or neutralized, for instance the poly(2-acrylamido-2-methylpropanesulfonic acid) marketed by Hoechst under the trademark Hostacerin AMPS (CTFA name: ammonium polyacryloyldimethyltaurate) or Simulgel 800 marketed by SEPPIC (CTFA name: sodium polyacryloyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 marketed by SEPPIC; cellulose-based derivatives such as hydroxyethylcellulose; polysaccharides and especially gums such as xanthan gum; and mixtures thereof.

Lipophilic thickeners that are exemplary include synthetic polymers such as poly($C_{10}$-$C_{30}$ alkyl acrylates) marketed under the trademark Intelimer IPA 13-1 and Intelimer IPA 13-6 by Landec, or modified clays such as hectorite and its derivatives, for instance the products marketed under the trademark Bentone.

Again, one skilled in this art will take care to select the optional additional compound(s) mentioned above and/or the amounts thereof such that the advantageous properties intrinsically associated with the compositions in accordance with the invention are not, or are not substantially, adversely affected by the envisaged addition(s), especially the improvement in the photostability of the dibenzoylmethane derivative.

The compositions according to the invention may be formulated according to techniques that are well known to one skilled in this art. They may be in particular in the form of a simple or complex emulsion (O/W, W/O, O/W/O or W/O/W emulsion) such as a cream, a milk or a cream-gel; in the form of an aqueous gel; in the form of a lotion. They may optionally be packaged as an aerosol and may be in the form of a mousse or a spray.

The compositions according to the invention are preferably in the form of an oil-in-water or water-in-oil emulsion.

The emulsions generally contain at least one emulsifier selected from among amphoteric, anionic, cationic and nonionic emulsifiers, which are used alone or as a mixture. The emulsifiers are appropriately selected according to the emulsion to be obtained (W/O or O/W). The emulsions may also contain stabilizers of other types, for instance fillers, gelling polymers or thickeners.

As emulsifying surfactants that may be used for the preparation of the W/O emulsions, examples include sorbitan, glycerol or sugar alkyl esters or ethers; silicone surfactants, for instance dimethicone copolyols, such as the mixture of cyclomethicone and of dimethicone copolyol, marketed under the trademark DC 5225 C by Dow Corning, and alkyldimethicone copolyols such as laurylmethicone copolyol marketed under the trademark Dow Corning 5200 Formulation Aid by Dow Corning; cetyldimethicone copolyol, such as the product marketed under the trademark Abil EM 90R by Goldschmidt, and the mixture of cetyldimethicone copolyol, of polyglyceryl isostearate (4 mol) and of hexyl laurate, marketed under the trademark Abil WE O9 by Goldschmidt. One or more co-emulsifiers may also be added thereto, which may be selected advantageously from the group comprising polyol alkyl esters.

Polyol alkyl esters that are especially exemplary include polyethylene glycol esters, for instance PEG-30 dipolyhydroxystearate, such as the product marketed under the trademark Arlacel P135 by ICI.

Glycerol and/or sorbitan esters that are especially exemplary include, for example, polyglyceryl isostearate, such as the product marketed under the trademark Isolan GI 34 by Goldschmidt, sorbitan isostearate, such as the product marketed under the trademark Arlacel 987 by ICI, sorbitan glyceryl isostearate, such as the product marketed under the trademark Arlacel 986 by ICI, and mixtures thereof.

For the O/W emulsions, examples of emulsifiers include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters, for instance the mixture PEG-100 stearate/glyceryl stearate marketed, for example, by ICI under the trademark Arlacel 165; oxyalkylenated (oxyethylenated and/or oxypropylenated) fatty alkyl ethers; sugar esters, for instance sucrose stearate; fatty alkyl ethers of sugars, especially polyalkylglucosides (APG) such as decylglucoside and laurylglucoside marketed, for example, by Henkel under the respective names Plantaren 2000 and Plantaren 1200, cetostearyl glucoside optionally as a mixture with cetostearyl alcohol, marketed, for example, under the trademark Montanov 68 by SEPPIC, under the trademark Tegocare CG90 by Goldschmidt and under the trademark Emulgade KE3302 by Henkel, and also arachidyl glucoside, for example in the form of a mixture of arachidyl alcohol, behenyl alcohol and arachidyl glucoside, marketed under the trademark Montanov 202 by SEPPIC. According to one particular embodiment of the invention, the mixture of the alkylpolyglucoside as defined above with the corresponding fatty alcohol may be in the form of a self-emulsifying composition as described, for example, in WO-A-92/06778.

Among the other emulsion stabilizers that will be used more particularly are isophthalic acid or sulfoisophthalic acid polymers, and in particular phthalate/sulfoisophthalate/glycol copolymers, for example the diethylene glycol/phthalate/isophthalate/1,4-cyclohexanedimethanol copolymer (INCI name: Polyester-5) marketed under the trademark Eastman AQ Polymer (AQ35S, AQ38S, AQ55S and AQ48 Ultra) by Eastman Chemical.

When it is an emulsion, the aqueous phase of this emulsion may comprise a nonionic vesicular dispersion prepared according to known processes (Bangham, Standish and Watkins, J. Mol. Biol., 13, 238 (1965), FR-2,315,991 and FR-2,416,008).

The compositions according to the invention find application in a large number of treatments, especially cosmetic treatments, of the skin, the lips and the hair, including the scalp, especially for protecting and/or caring for the skin, the lips and/or the hair, and/or for making up the skin and/or the lips.

Another aspect of the present invention consists of the use of the compositions according to the invention as defined above for the manufacture of cosmetic products for treating the skin, the lips, the nails, the hair, the eyelashes, the eyebrows and/or the scalp, especially care products, anti-sun products and makeup products.

The cosmetic compositions according to the invention may be used, for example, as makeup products.

The cosmetic compositions according to the invention may be used, for example, as care products and/or anti-sun protection products for the face and/or the body, of liquid to semi-liquid consistency, such as milks, more or less rich creams, cream-gels and pastes. They may optionally be conditioned in aerosol form and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to one skilled in this art and comprise non-aerosol pumps or "atomizers", aerosol containers comprising a propellant and also aerosol pumps using compressed air as propellant. These devices are described in U.S. Pat. Nos. 4,077,441 and 4,850,517 (incorporated by reference herein).

The compositions conditioned in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. These are preferably present in amounts ranging from 15% to 50% by weight relative to the total weight of the composition.

The compositions according to the invention may also comprise additional cosmetic or dermatological active agents.

The additional active agents may be selected especially from among moisturizers, desquamating agents, agents for improving the skin barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, tensioning agents, lipo-restructuring agents, slimming agents, agents for promoting the cutaneous capillary circulation, calmatives and/or anti-irritants, sebo-regulators or anti-seborrhoeic agents, astringents, cicatrizing agents, anti-inflammatory agents and anti-acne agents.

One skilled in this art will select the said active agent(s) as a function of the effect desired on the skin, the hair, the eyelashes, the eyebrows and the nails.

For caring for and/or making up aged skin, one will preferably select at least one active agent selected from among moisturizers, desquamating agents, agents for improving the barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, and agents for promoting the cutaneous microcirculation for the area around the eyes.

The composition may also comprise at least one ingredient such as fillers with a soft-focus effect or agents for promoting the natural coloration of the skin, useful for complementing the biological effects of these active agents or for providing an immediate visual anti-aging effect.

For caring for and/or making up greasy skin, one skilled in this art will preferably select at least one active agent selected from among desquamating agents, sebo-regulating agents or anti-seborrhoeic agents, and astringents.

The composition may also comprise at least one additional ingredient for complementing the biological effect of these active agents or for providing an immediate visual effect; especially exemplary are matting agents, fillers with a soft-focus effect, fluorescers, agents for promoting the naturally pinkish coloration of the skin, and abrasive fillers or exfoliants.

Moisturizers or Humectants:

Moisturizers or humectants that are especially exemplary include glycerol and derivatives thereof, urea and derivatives thereof, especially Hydrovance® marketed by National Starch, lactic acid, hyaluronic acid, AHAs, BHAs, sodium pidolate, xylitol, serine, sodium lactate, ectoin and derivatives thereof, chitosan and derivatives thereof, collagen, plankton, an extract of *Imperata cylindra* marketed under the trademark Moist 24® by Sederma, acrylic acid homopolymers, for instance Lipidure-HM® from NOF Corporation, beta-glucan from Mibelle-AG-Biochemistry; a mixture of passionflower oil, apricot oil, corn oil and rice bran oil marketed by Nestlé under the trademark NutraLipids®; a C-glycoside derivative such as those described in WO 02/051 828 and in particular C-β-D-xylopyranoside-2-hydroxypropane in the form of a solution containing 30% by weight of active material in a water/propylene glycol mixture (60/40% by weight) such as the product marketed by Chimex under the trademark Mexoryl SBB®; an oil of musk rose marketed by Nestlé; an oil of the microalga *Prophyridium cruentum* enriched with zinc, marketed by Vincience under the trademark Algualane Zinc®; spheres of collagen and of chondroitin sulfate of marine origin (Atelocollagen) marketed by Engelhard Lyon under the trademark Marine Filling Spheres; hyaluronic acid spheres such as those marketed by Engelhard Lyon; and arginine.

The moisturizer that will preferably be employed is selected from among urea and derivatives thereof, especially Hydrovance® marketed by National Starch, hyaluronic acid, AHAs, BHAs, acrylic acid homopolymers, for instance Lipidure-HM® from NOF Corporation, beta-glucan from Mibelle-AG-Biochemistry; a mixture of passionflower oil, apricot oil, corn oil and rice bran oil marketed by Nestlé under the trademark NutraLipids®; a C-glycoside derivative such as those described in WO 02/051 828 and in particular C-β-D-xylopyranoside-2-hydroxypropane in the form of a solution containing 30% by weight of active material in a water/propylene glycol mixture (60/40% by weight) such as the product marketed by Chimex under the trademark Mexoryl SBB®; an oil of musk rose marketed by Nestlé; an oil of the microalga *Prophyridium cruentum* enriched with zinc, marketed by Vincience under the trademark Algualane Zinc®; spheres of collagen and of chondroitin sulfate of marine origin (Atelocollagen) marketed by Engelhard Lyon under the trademark Marine Filling Spheres; hyaluronic acid spheres such as those marketed by Engelhard Lyon; and arginine.

Desquamating Agents:

The term "desquamating agent" means any compound capable of acting:

either directly on desquamation by promoting exfoliation, such as β-hydroxy acids (BHA), in particular salicylic acid and derivatives thereof (including 5-n-octanoylsalicylic acid, also known as capryloyl salicylic acid as the INCI name); α-hydroxy acids (AHA), such as glycolic acid, citric acid, lactic acid, tartaric acid, malic acid or mandelic acid; 8-hexadecene-1,16-dicarboxylic acid or 9-octadecenedioic acid; gentisic acid and derivatives thereof; oligofucoses; cinnamic acid; *Saphora japonica* extract; resveratrol, and certain jasmonic acid derivatives;

or on the enzymes involved in the desquamation or degradation of corneodesmosomes, glycosidases, stratum corneum chymotryptic enzyme (SCCE) or other proteases (trypsin, chymotrypsin-like). Exemplary are aminosulfonic compounds and in particular 4-(2-hydroxyethyl)piperazine-1-propanesulfonic acid (HEPES); 2-oxothiazolidine-4-carboxylic acid (procysteine) derivatives; derivatives of α-amino acids of glycine type (as described in EP-0,852,949, and also sodium methyl glycine diacetate marketed by BASF under the trademark Trilon M); honey; O-octanoyl-6-D-maltose and N-acetylglucosamine.

As other desquamating agents that may be included in the compositions according to the invention, exemplary are:

oligofructoses, EDTA and derivatives thereof, laminaria extracts, o-linoleyl-6D-glucose, (3-hydroxy-2-pentylcyclopentyl)acetic acid, glycerol trilactate, O-octanyl-6'-D-maltose, S-carboxymethylcysteine, siliceous derivatives of salicylate such as those described in EP-0,796,861, oligofucases such as those described in EP-0,218,200, 5-acyl salicylic acid salts, active agents with effects on transglutaminase, as in EP-0,899,330, extract of the flowers of ficus *Opuntia indica* (Exfolactive® from Silab), 8-hexadecene-1,16-dicarboxylic acid, esters of glucose and of vitamin F, and mixtures thereof.

Preferred desquamating agents include β-hydroxy acids such as 5-n-octanoyl salicylic acid; urea; glycolic acid, citric acid, lactic acid, tartaric acid, malic acid or mandelic acid; 4-(2-hydroxyethyl)piperazine-1-propanesulfonic acid (HEPES); extract of *Saphora japonica*; honey; N-acetyl glucosamine; sodium methyl glycine diacetate, and mixtures thereof.

Even more preferentially, a desquamating agent selected from among 5-n-octanoyl salicylic acid; urea; 4-(2-hydroxyethyl)piperazine-1-propanesulfonic acid (HEPES); extract of *Saphora japonica*; honey; N-acetyl glucosamine; sodium methyl glycine diacetate, and mixtures thereof, will be included in the compositions of the invention.

Agents for Improving the Barrier Function:

As agents for improving the barrier function, exemplary are arginine, an extract of *Thermus thermophilus* such as Venuceane® from Sederma, an extract of the rhizome of wild yam (*Dioscorea villosa*) such as Actigen Y® from Active Organics, plankton extracts, for instance Omega Plankton® from Secma, yeast extracts, for instance Relipidium® from Coletica, a chestnut extract such as Recoverine® from Silab, a cedar bud extract such as Gatuline Zen® from Gattefossé, sphingosines, for instance salicyloyl sphingosine marketed under the trademark Phytosphingosine® SLC by Degussa, a mixture of xylitol, polyxylityl glycoside and xylitan, for instance Aquaxyl® from SEPPIC, extracts of Solanacea plants, for instance Lipidessence® from Coletica, omega-3 unsaturated oils such as musk rose oils, and mixtures thereof.

Especially exemplary are ceramides or derivatives thereof, in particular ceramides of type 2 (for instance N-oleoyldihydrosphingosine), of type 3 (for instance stearoyl-4-hydroxysphinganine, as the INCI name) and of type 5 (for instance N-2-hydroxypalmitoyldihydrosphingosine, having the INCI name: hydroxypalmitoyl sphinganine), sphingoid-based compounds, glycosphingolipids, phospholipids, cholesterol and derivatives thereof, phytosterols, essential fatty acids, diacylglycerol, 4-chromanone and chromone derivatives, petroleum jelly, lanolin, shea butter, cocoa butter, lanolin and PCA salts.

Preferred agents having a restructuring effect on the barrier function include an extract of *Thermus thermophilus*, an extract of wild yam rhizome (*Dioscorea villosa*), a yeast extract, a chestnut extract, a cedar bud extract, arginine, ceramides especially of type 3 and 5; and mixtures thereof.

Preferably, serine or arginine, or a mixture thereof, will be used.

Depigmenting Agents:

Depigmenting agents that are especially exemplary include vitamin C and derivatives thereof and especially vitamin CG, CP and 3-O ethyl vitamin C, alpha and beta arbutin, ferulic acid, lucinol and derivatives thereof, kojic acid, resorcinol and derivatives thereof, tranexamic acid and derivatives thereof, gentisic acid, homogentisate, methyl gentisate or homogentisate, dioic acid, calcium D-pantheteine sulfonate, lipoic acid, ellagic acid, vitamin B3, linoleic acid and derivatives thereof, ceramides and homologues thereof, plant derivatives, for instance camomile, bearberry, the aloe family (vera, ferox, bardensis), mulberry or skullcap; a kiwi fruit (*Actinidia chinensis*) juice marketed by Gattefossé, an extract of *Paeonia suffruticosa* root, such as the product marketed by Ichimaru Pharcos under the trademark Botanpi Liquid B®, an extract of brown sugar (*Saccharum officinarum*), such as the extract of molasses marketed by Taiyo Kagaku under the trademark Molasses Liquid, without this list being exhaustive.

Vitamin C and derivatives thereof and especially vitamin CG, CP and 3-O ethyl vitamin C, alpha and beta arbutin, ferulic acid, kojic acid, resorcinol and derivatives thereof, calcium D-pantheteine sulfonate, lipoic acid, ellagic acid, vitamin B3, a kiwi fruit (*Actinidia chinensis*) juice marketed by Gattefosse, and an extract of *Paeonia suffruticosa* root, such as the product marketed by Ichimaru Pharcos under the trademark Botanpi Liquid B®, will be used as preferred depigmenting agents.

Antioxidants:

Especially exemplary are tocopherol and esters thereof, in particular tocopheryl acetate; ascorbic acid and derivatives thereof, in particular magnesium ascorbyl phosphate and ascorbyl glucoside; ferulic acid; serine; ellagic acid, polyphenols, tannins, tannic acid, epigallocatechins and natural extracts containing them, anthocyans, rosemary extracts, olive leaf extracts, for instance those from the company Silab, green tea extracts, resveratrol and derivatives thereof, ergothioneine, N-acetylcysteine, an extract of the brown alga *Pelvetia caniculata*, for instance Pelvetiane® from Secma, chlorogenic acid, biotin, chelating agents, such as BHT and BHA, N,N'-bis(3,4,5-trimethoxybenzyl)ethylenediamine and salts thereof; idebenone, plant extracts, for instance Pronalen Bioprotect™ from the company Provital; coenzyme Q10, bioflavonoids, SODs, phytanetriol, lignans, melatonin, pidolates, glutathione, caprylyl glycol, phloretin, Totarol™ or extract of *Podocarpus totara* containing Totarol (totara-8,11,13-trienol or 2-phenanthrenol, 4b,5,6,7,8,8a,9,10-octahydro-4-b,8,8-trimethyl-1-(1-methylethyl)-; a jasmine extract such as the product marketed by Silab under the trademark Helisun®; hesperitin laurate such as Flavagrum PEG® from the company Engelhard Lyon; an extract of *Paeonia suffruticosa* root, such as the product marketed by Ichimaru Pharcos under the trademark Botanpi Liquid B®, an extract of lychee such as the extract of lychee pericarp marketed by Cognis under the trademark Litchiderm LS 9704®, an extract of pomegranate fruit (*Punica granatum*), such as the product marketed by Draco Natural Products.

Other anti-aging agents that are exemplary include DHEA and derivatives thereof, boswellic acid, rosemary extracts, carotenoids (β-carotene, zeaxanthin and lutein), cysteic acid, copper derivatives and jasmonic acid.

Preferred antioxidants include ferulic acid; serine; phloretin, an extract of pomegranate, biotin, chelating agents such as BHT, BHA, N,N'-bis(3,4,5-trimethoxybenzyl)ethylenediamine and salts thereof; caprylyl glycol, phloretin, Totarol™, a jasmine extract such as the product marketed by Silab under the trademark Helisun®; hesperitin laurate such as Flavagrum PEG® from the company Engelhard Lyon; an extract of *Paeonia suffruticosa* root, such as the product marketed by Ichimaru Pharcos under the trademark Botanpi Liquid B®.

Dermo-Relaxing or Dermo-Decontracting Agents:

Examples thereof include manganese gluconate and other salts, adenosine, alverine citrate and salts thereof, lysine, an extract of *Iris pallida*, a hexapeptide (Argeriline R from Lipotec) or sapogenins, for instance wild yam and the carbonyl amines described in EP-1,484,052. Examples of sapogenins include those described in WO 02/47650, in particular wild yam, the diosgenin extracted especially from *Dioscorea opposita* or any extract naturally containing or containing after treatment one or more sapogenins (wild yam rhizome, agave leaf, which contains hecogenin and tigogenin, extracts of Liliacea plants and more particularly yucca or smilax containing smilagenin and sarsapogenin, or sarsaparilla) or Actigen Y from the company Actives Organics, or ginger.

Also exemplary are DMAE (dimethyl MEA), extracts of sea fennel, of rockrose, of *helichrysum*, of aniseed, of paracress, and an extract of *Acmella oleracea*, for instance Gatuline® from Gattefossé.

Preferred dermo-relaxing agents include adenosine, manganese gluconate, wild yam, sea fennel, glycine and alverine.

Anti-Glycation Agents:

The term "anti-glycation agent" means a compound that prevents and/or reduces the glycation of skin proteins, in particular dermal proteins such as collagen.

Anti-glycation agents that are exemplary include extracts of plants of the Ericacea family, such as an extract of blueberry (*Vaccinium angustifolium* or *Vaccinium myrtillus*), for example the product marketed under the trademark Blueberry Herbasol Extract PG by Cosmetochem, ergothioneine and derivatives thereof, hydroxystilbenes and derivatives thereof, such as resveratrol and 3,3',5,5'-tetrahydroxystilbene (these anti-glycation agents are described in FR-2,802,425, FR-2,810,548, FR-2,796,278 and FR-2,802,420, respectively), dihydroxystilbenes and derivatives thereof, polypeptides of arginine and of lysine such as the product marketed under the trademark Amadorine® by Solabia, carsinine hydrochloride (marketed by Exsymol under the trademark Alistin®), an extract of *Helianthus annuus*, for instance Antiglyskin® from Silab, wine extracts such as the extract of powdered white wine on a maltodextrin support marketed under the trademark Vin blanc déshydraté 2F by Givaudan, thioctic acid (or alpha-lipoic acid), a mixture of extract of bearberry and of marine glycogen, for instance Aglycal LS 8777® from Laboratoires Sérobiologiques, and an extract of black tea, for instance Kombuchka® from Sederma, and mixtures thereof.

Preferred anti-glycation agents include extracts of blueberry (*Vaccinium myrtillus*) and extracts of black tea.

Agents for Stimulating the Synthesis of Dermal and/or Epidermal Macromolecules and/or for Preventing their Degradation:

Among the active agents for stimulating the dermal macromolecules or for preventing their degradation, exemplary are those acting:

either on collagen synthesis, such as extracts of *Centella asiatica*, asiaticosides and derivatives thereof; ascorbic acid or vitamin C and derivatives thereof; synthetic peptides such as iamin, biopeptide CL or palmitoyl oligopeptide marketed by Sederma; peptides extracted from plants, such as the soybean hydrolysate marketed by Coletica under the trademark Phytokine®; rice peptides such as Nutripeptide® from Silab, methylsilanol mannuronate such as Algisium C® marketed by Exsymol; plant hormones such as auxins and lignans; folic acid; and an extract of *Medicago sativa* (alfalfa) such as the product marketed by Silab under the trademark Vitanol®; a peptide extract of hazelnut such as the product marketed by Solabia under the trademark Nuteline C®; and arginine;

or on the inhibition of collagen degradation, in particular agents acting on the inhibition of metalloproteases (MMP) more particularly such as MMP 1, 2, 3 and 9. Exemplary are retinoids and derivatives, extracts of *Medicago sativa* such as Vitanol® from Silab, an extract of *Aphanizomenon flos-aquae* (Cyanophyceae) marketed under the trademark Lanablue® by Atrium Biotechnologies, oligopeptides and lipopeptides, lipoamino acids, the malt extract marketed by Coletica under the trademark Collalift®; blueberry or rosemary extracts; lycopene; isoflavones, derivatives thereof or plant extracts containing them, in particular extracts of soybean (marketed, for example, by Ichimaru Pharcos under the trademark Flavosterone SB®), of red clover, of flax or of kakkon; an extract of lychee such as the extract of lychee pericarp marketed by Cognis under the trademark Litchiderm LS 9704®; Dipalmitoyl Hydroxyproline marketed by SEPPIC under the trademark Sepilift DPHP®: *Baccharis genistelloides* or Baccharine marketed by Silab, an extract of moringa such as Arganyl LS 9781® from Cognis; the sage extract described in FR-A-2,812,544 from the Labiatae family (*Salvia officinalis* from the company Flacksmann), an extract of rhododendron, a blueberry extract, and an extract of *Vaccinium myrtillus* such as those described in FR-A-2,814,950;

or on the synthesis of molecules belonging to the elastin family (elastin and fibrillin), such as: retinol and derivatives, in particular retinyl palmitate; the extract of *Saccharomyces cerevisiae* marketed by LSN under the trademark Cytovitin®; and the extract of the alga *Macrocystis pyrifera* marketed by Secma under the trademark Kelpadelie®; a peptide extract of hazelnut such as the product marketed by Solabia under the trademark Nuteline C®;

or on inhibition of elastin degradation, such as the peptide extract of seeds of *Pisum sativum* marketed by LSN under the trademark Parelastyl®; heparinoids; and the N-acylamino acid compounds described in WO 01/94381, such as {2-[acetyl(3-trifluoromethylphenyl)amino]-3-methylbutyrylamino}acetic acid, also known as N—[N-acetyl, N'-(3-trifluoromethyl)phenylvalyl]glycine, or N-acetyl-N-[3-(trifluoromethyl)phenyl]valyl glycine or acetyl trifluoromethyl phenyl valylglycine, or an ester thereof with a $C_1$-$C_6$ alcohol; an extract of rice peptides such as Colhibin® from Pentapharm, or an extract of *Phyllanthus emblica* such as Emblica® from Rona;

or on the synthesis of glycosaminoglycans, such as the product of fermentation of milk with *Lactobacillus vulgaris*, marketed by Brooks under the trademark Biomin Yoghurt®; the extract of the brown alga *Padina pavonica* marketed by Alban Müller under the trademark HSP3®; the *Saccharomyces cerevisiae* extract available especially from the company Silab under the trademark Firmalift® or from the company LSN under the trademark Cytovitin®; an extract of *Laminaria ochroleuca* such as Laminaine® from Secma; essence of Mamaku from Lucas Meyer, and an extract of Cress (Odraline® from Silab);

or on the synthesis of fibronectin, such as the extract of the zooplankton Salina marketed by Seporga under the trademark GP4G®; the yeast extract available especially from the company Alban Müller under the trademark Drieline®; and the palmitoyl pentapeptide marketed by Sederma under the trademark Matrixyl®.

Among the active agents for stimulating epidermal macromolecules, such as fillagrin and keratins, especially exemplary are the extract of lupin marketed by Silab under the trademark Structurine®; the extract of *Fagus sylvatica* beech buds marketed by Gattefossé under the trademark Gatuline® RC; and the extract of the zooplankton Salina marketed by Seporga under the trademark GP4G®; the copper tripeptide from Procyte; a peptide extract of *Voandzeia substerranea* such as the product marketed by Laboratoires Sérobiologiques under the trademark Filladyn LS 9397®.

Preferably, an active agent that stimulates the synthesis of dermal and/or epidermal macromolecules and/or that prevents their degradation, selected from among agents for stimulating the synthesis of glycosaminoglycans, agents for inhibiting elastin degradation, agents for stimulating fibronectin synthesis, agents for stimulating the synthesis of epidermal macromolecules, and mixtures thereof, will preferably be used.

Even more preferentially, an active agent that stimulates the synthesis of the glycosaminoglycans, selected from among an extract of the brown alga *Padina pavonica*, an extract of *Saccharomyces cerevisiae*, an extract of *Laminaria ochroleuca*, essence of Mamaku, and an extract of cress, and mixtures thereof, will even more preferentially be used.

As preferred active agents for stimulating the synthesis of dermal and/or epidermal macromolecules and/or for preventing their degradation, exemplary are:

synthetic peptides such as iamin, the biopeptide CL or palmitoyloligopeptide marketed by Sederma; peptides extracted from plants, such as the soybean hydrolysate marketed by Coletica under the trademark Phytokine®; rice peptides such as Nutripeptide® from Silab, methylsilanol mannuronate such as Algisium C® marketed by Exsymol; folic acid; an extract of *Medicago sativa* (alfalfa), such as the product marketed by Silab under the trademark Vitanol®; a peptide extract of hazelnut, such as the product marketed by Solabia under the trademark Nuteline C®; arginine; an extract of *Aphanizomenon flos-aquae* (Cyanophyceae) marketed under the trademark Lanablue® by Atrium Biotechnologies, the malt extract marketed by Coletica under the trademark Collalift®, lycopene; an extract of lychee; an extract of moringa such as Arganyl LS 9781® from Cognis; an extract of *Vaccinium myrtillus* such as those described in FR-A-2,814,950; retinol and derivatives thereof, in particular retinyl palmitate; the extract of *Saccharomyces cerevisiae* marketed by LSN under the trademark Cytovitin®; a peptide extract of hazelnut such as the product marketed by Solabia under the trademark Nuteline C®; {2-[acetyl(3-trifluoromethylphenyl)amino]-3-methylbutyrylamino}acetic acid, also known as N—[N-acetyl, N'-(3-trifluoromethyl)phenylvalyl] glycine, or N-acetyl-N-[3-(trifluoromethyl)phenyl]valyl glycine or acetyl trifluoromethyl phenyl valylglycine, or an ester thereof with a $C_1$-$C_6$ alcohol; an extract of rice peptides such as Colhibin® from Pentapharm, or an extract of *Phyllanthus emblica* such as Emblica® from Rona; the extract of the brown alga *Padina pavonica* marketed by Alban Müller under the trademark HSP3®; the extract of *Saccharomyces cerevisiae* available especially from the company Silab under the trademark Firmalift® or from the company LSN under the trademark Cytovitin®; an extract of *Laminaria ochroleuca* such as Laminaine® from Secma; the essence of Mamaku from Lucas Meyer, the extract of lupin marketed by Silab under the trademark Structurine®; the extract of *Fagus sylvatica* beech buds marketed by Gattefossé under the trademark Gatuline® RC.

Agents for Stimulating Fibroblast or Keratinocyte Proliferation and/or Keratinocyte Differentiation:

The agents for stimulating fibroblast proliferation that may be included in the compositions according to the invention may be selected, for example, from plant proteins or polypeptides, extracted especially from soybean (for example a soybean extract marketed by LSN under the trademark Eleseryl SH-VEG 8® or marketed by Silab under the trademark Raffermine®); an extract of hydrolyzed soybean proteins such as Ridulisse® from Silab; and plant hormones such as gibberellins and cytokinins; a peptide extract of hazelnut such as the product marketed by Solabia under the trademark Nuteline C®.

Preferably, an agent that promotes keratinocyte proliferation and/or differentiation will be formulated.

The agents for stimulating keratinocyte proliferation that may be included in the compositions according to the invention especially comprise adenosine; phloroglucinol, the extract of *Hydrangea macrophylla* leaves, for instance Amacha Liquid E® from Ichimaru Pharcos, a yeast extract such as Stimoderm® from CLR; the extract of *Larrea divaricata* such as Capislow® from Sederma, mixtures of extract of papaya, of olive leaves and of lemon, such as Xyleine® from Vincience, the extract of *Hydrangea macrophylla* leaves, for instance Amacha Liquid E® from Ichimaru Pharcos, retinol and esters thereof, including retinyl palmitate, phloroglucinol, the nut cake extracts marketed by the Gattefossé and the extracts of *Solanum tuberosum* such as Dermolectine® marketed by Sederma.

The agents for stimulating keratinocyte differentiation are, for example, minerals such as calcium; sea fennel, a peptide extract of lupin, such as the product marketed by Silab under the trademark Structurine®; sodium beta-sitosteryl sulfate, such as the product marketed by Seporga under the trademark Phytocohesine®; and a water-soluble extract of corn, such as the product marketed by Solabia under the trademark Phytovityl®; a peptide extract of *Voandzeia substerranea* such as the product marketed by Laboratoires Sérobiologiques under the trademark Filladyn LS 9397®; and lignans such as secoisolariciresinol, and retinol and esters thereof, including retinyl palmitate.

Agents for stimulating keratinocyte proliferation and/or differentiation include the oestrogens such as oestradiol and homologues; cytokines.

Preferred active agents for stimulating fibroblast or keratinocyte proliferation and/or keratinocyte differentiation include the plant proteins or polypeptides, extracted especially from soybean (for example a soybean extract marketed by LSN under the trademark Eleseryl SH-VEG 8® or marketed by Silab under the trademark Raffermine®); an extract of hydrolyzed soybean proteins such as Ridulisse® from Silab; a peptide extract of hazelnut such as the product marketed by Solabia under the trademark Nuteline C®; adenosine; phloroglucinol, a yeast extract such as Stimoderm® from CLR; a peptide extract of lupin such as the product marketed by Silab under the trademark Structurine®; a water-soluble corn extract, such as the product marketed by Solabia under the trademark Phytovityl®; a peptide extract of *Voandzeia substerranea*, such as the product marketed by Laboratoires Sérobiologiques under the trademark Filladyn LS 9397®; retinol and esters thereof, including retinyl palmitate.

Agents for Promoting the Maturation of the Horny Envelope

Agents that participate in the maturation of the horny envelope, which becomes impaired with age and induces a decrease in transglutaminase activity that may be included in the compositions of the invention, include urea and derivatives thereof and in particular Hydrovance® from National Starch and the other active agents indicated in L'Oréal FR-2,877,220 (unpublished).

NO-Synthase Inhibitors:

The agent with an inhibitory action on NO synthase may be selected from among OPCs (procyannidol oligomers); plant extracts of the species *Vitis vinifera* marketed especially by Euromed under the trademark "Leucocyanidines de raisins extra", or by Indena under the trademark Leucoselect®, or finally by Hansen under the trademark "Extrait de marc de raisin"; plant extracts of the species *Olea europaea* preferably obtained from olive tree leaves and marketed especially by Vinyals in the form of a dry extract, or by Biologia & Technologia under the trademark Eurol® BT; and plant extracts of the species *Gingko biloba*, preferably a dry aqueous extract of this plant marketed by Beaufour under the trademark "*Ginkgo biloba* extract standard", and mixtures thereof.

Peripheral Benzodiazepine Receptor (PBR) Antagonists:

Exemplary is 1-(2-chlorophenyl)-N-(1-methylpropyl)-3-isoquinoline carboxamide; the compounds described in WO 03/030 937 and WO 03/068 753, pyridazino[4,5-b]indole-1-acetamide derivatives of general formula (VII) as described in WO 00/44384.

Agents for Increasing the Activity of the Sebaceous Glands:

Exemplary are methyl dehydrojasmonate, hecogenin, hedione and O-linoleyl-6D-glucose, and mixtures thereof.

Agents for Stimulating the Energy Metabolism of Cells:

The active agent for stimulating the energy metabolism of cells may be selected, for example, from among biotin, an extract of *Saccharomyces cerevisiae* such as Phosphovital® from Sederma, the mixture of sodium, manganese, zinc and magnesium salts of pyrrolidonecarboxylic acid, for instance Physiogenyl® from Solabia, a mixture of zinc, copper and magnesium gluconate, such as Sepitonic M3® from SEPPIC, and mixtures thereof; a beta-glucan derived from *Saccharomyces cerevisiae*, such as the product marketed by Mibelle AG Biochemistry.

Tensioning Agents:

The term "tensioning agent" that may be included according to the invention means compounds liable to have a tensioning effect, i.e., being able to make the skin taut.

According to the invention, the term "tensioning agent" generally means any polymer that is soluble or dispersible in water at a temperature ranging from 25° C. to 50° C. at a concentration of 7% by weight in water or at the maximum concentration at which a medium of uniform appearance is formed and producing at this concentration of 7% or at this maximum concentration in water a shrinkage of more than 15% in the test described below.

The maximum concentration at which a medium of uniform appearance forms is determined to within ±10% to preferably to within ±5%.

The expression "medium of uniform appearance" means a medium that does not contain any aggregates that are visible to the naked eye.

For the determination of the said maximum concentration, the tensioning agent is gradually added to the water with deflocculating stirring at a temperature ranging from 25° C. to 50° C., and the mixture is then stirred for one hour. The mixture thus prepared is then examined after 24 hours to see if it is of uniform appearance (absence of aggregates visible to the naked eye).

The tensioning effect may be characterized by an in vitro shrinkage test.

A homogeneous mixture of the tensioning agent in water, at a concentration of 7% by weight or at the maximum concentration defined above, is prepared beforehand and as described previously.

30 µl of the homogeneous mixture are placed on a rectangular sample (10×40 mm, thus having an initial width $L_o$ of 10 mm) of elastomer with a modulus of 20 MPa and a thickness of 100 µm.

After drying for 3 hours at 22±3° C. and 40±10% relative humidity RH, the elastomer sample has a shrunken width, noted $L_{3h}$, due to the tension exerted by the applied tensioning agent.

The tensioning effect (TE) of the said polymer is then quantified in the following manner:

$$'TE' = (L_0 - L_{3h}/L_0) \times 100 \text{ as } \%$$

with $L_0$=initial width 10 mm and
$L_{3h}$=width after 3 hours of drying.

The tensioning agent may be selected from among:
plant or animal proteins and hydrolysates thereof;
polysaccharides of natural origin;
mixed silicates;
colloidal particles of mineral fillers;
synthetic polymers;
and mixtures thereof.

One skilled in this art will know how to select, from the chemical categories listed above, the materials corresponding to the tensioning test as described below.

Especially exemplary are:

(a) plant proteins and protein hydrolysates, in particular of corn, rye, wheat, buckwheat, sesame, spelt, pea, bean, lentil, soybean and lupin, (b) polysaccharides of natural origin, especially (a) polyholosides, for example (i) in the form of starch derived especially from rice, corn, potato, cassava, pea, wheat, oat, etc. or (ii) in the form of carrageenans, alginates, agars, gellans, cellulose polymers and pectins, advantageously as an aqueous dispersion of gel microparticles, and (b) latices consisting of shellac resin, sandarac gum, dammar resins, elemi gums, copal resins, cellulose derivatives, and mixtures thereof, (c) mixed silicates, especially phyllosilicates and in particular Laponites, (d) colloidal particles of mineral fillers with a number-average diameter of from 0.1 and 100 nm and preferably from 3 and 30 nm, and selected, for example, from: silica, silica-alumina composites, cerium oxide, zirconium oxide, alumina, calcium carbonate, barium sulfate, calcium sulfate, zinc oxide and titanium dioxide. As silica-alumina composite colloidal particles that may be included in the compositions according to the invention, examples include those marketed by Grace under the trademarks Ludox AM, Ludox AM-X 6021, Ludox HSA and Ludox TMA, (e) synthetic polymers, such as polyurethane latices or acrylic-silicone latices, in particular those described in EP-1, 038,519, such as a polydimethylsiloxane grafted with propylthio(polymethyl acrylate), propylthio(polymethyl methacrylate) and propylthio(polymethacrylic acid), or, alternatively, a polydimethylsiloxane grafted with propylthio (polyisobutyl methacrylate) and propylthio(polymethacrylic acid). Such grafted silicone polymers are especially marketed by 3M under the trademarks VS 80, VS 70 and LO21.

The tensioning agent will be present in the composition in an amount that is effective for obtaining the desired biological effect according to the invention.

By way of example, the tensioning agent may be included in the composition according to the invention in a content ranging from 0.01% to 30% by weight of active material and preferably from 1% to 30% by weight of active material relative to the total weight of the composition.

The term "active material" is intended to exclude the medium in which the tensioning agent may be dissolved or dispersed in its commercial form, for example in the case of dispersions of colloidal particles.

It is also possible, especially to complement and/or potentiate the effect of tensioning agents, to use agents that increase the expression of mechanoreceptors, such as agents that increase the expression of integrins.

One example is an extract of rye seed, such as the product marketed by Silab under the trademark Coheliss®.

Fat-Restructuring Agents:

According to the invention, the term "fat-restructuring agents" means agents capable of stimulating lipogenesis and of promoting adipocyte differentiation, thus making it possible to prevent or slow down the wasting of fat contained in the skin supporting tissues, also known as "wasting of skin fat".

The term "skin fat" means the network of fat cells that form the volumes on which the facial skin rests and is molded.

These agents are useful to reduce the loss of skin density and/or the wasting of skin fat, in particular on the cheeks and around the eyes, and/or to prevent the collapse and/or hollowing of the facial volumes, the loss of consistency of the skin and/or its maintenance, in particular on the cheeks and around the eyes, and/or to improve the underlying volumes of the skin of the face and/or the neck, in particular on the cheeks, the oval of the face and around the eyes, and/or to improve the density, springiness and maintenance of the skin, in particular on the cheeks, the oval of the face and around the eyes, and/or to remodel the facial features, in particular the oval of the face.

Examples of fat-restructuring agents include an extract of black tea, such as the extract of fermented black tea marketed by Sederma under the trademark Kombuchka®, and an extract of *Artemisia abrotanum*, such as the product marketed by Silab under the trademark Pulpactyl®.

Slimming Agents:

Slimming (lipolytic) agents that are especially exemplary include theophylline and its derivatives, theobromine, acefylline, aminophylline, chloroethyltheophylline, diprofylline, diniprophylline, etamiphylline and its derivatives, etofylline and proxyphylline; extracts of tea, of coffee, of guarana, of maté, of cola (*Cola nitida*) and especially the dry extract of guarana fruit (*Paulina sorbilis*) containing 8% to 10% caffeine; extracts of climbing ivy (*Hedera helix*), of arnica (*Arnica montana* L), of rosemary (*Rosmarinus officinalis* N), of marigold (*Calendula officinalis*), of sage (*Salvia officinalis* L), of ginseng (*Panax ginseng*), of St.-John's wort (*Hypericum perforatum*), of butcher's-broom (*Ruscus aculeatus* L), of meadowsweet (*Filipendula ulmaria* L), of orthosiphon (*Orthosiphon stamincus Benth*), of birch (*Betula alba*), of pumpwood and of argan tree, extracts of ginkgo biloba, extracts of horsetail, extracts of escin, extracts of cangzhu, extracts of *Chrysanthellum indicum*, extracts of diosgenin-rich *Dioscorea* plants or pure diosgenin or hecogenin and derivatives thereof, extracts of Ballota, extracts of Guioa, of *Davallia*, of *Terminalia*, of *Barringtonia*, of *Trema* or of *Antirobia*, the extract of bitter orange pips; an extract of husks of cocoa beans (*Theobroma cacao*) such as the product marketed by Solabia under the trademark Caobromine®.

Agents for Promoting the Cutaneous Microcirculation:

The active agent acting on the cutaneous microcirculation may be included for preventing dulling of the complexion and/or to improve the appearance of the area around the eyes, in particular to reduce the shadows around the eyes. It may be selected, for example, from an extract of maritime pine bark, for instance Pycnogenol® from Biolandes, manganese gluconate (Givobio GMn® from SEPPIC), an extract of *Ammi visnaga* such as Visnadine from Indena, extract of lupin (Eclaline® from Silab), the protein coupling of hydrolyzed wheat/palmitic acid with palmitic acid, such as Epaline 100 from Laboratoires Cadléne, the extract of bitter orange blossom (Remoduline® from Silab), vitamin P and derivatives thereof, for instance methyl-4 esculetol sodium monoethanoate marketed under the trademark Permethol® by Sephytal, extracts of Ruscus, of common horse chestnut, of ivy, of ginseng and of melilot, caffeine, nicotinate and derivatives thereof, lysine and derivatives thereof, for instance Asparlyne® from Solabia, an extract of black tea such as Kombuchka from Sederma; rutin salts; an extract of the alga *Corallina officinalis*, such as the product marketed by Codif; and mixtures thereof.

Preferred agents for promoting the cutaneous microcirculation include caffeine, an extract of bitter orange blossom, an extract of black tea, rutin salts and an extract of the alga *Corallina officinalis*.

Calmatives or Anti-Irritants:

The term "calmative" means a compound that can reduce the sensation of stinging, itching or tautness of the skin.

As calmatives that may be included in the composition according to the invention include procyannidol oligomers, vitamins E, C, B5 and B3, caffeine and derivatives thereof, pentacylic triterpenes and plant extracts containing them, β-glycyrrhetinic acid and salts or derivatives thereof (stearyl glycyrrhetate, 3-stearoyloxyglycyrrhetic acid or glycyrrhetinic acid monoglucuronide) and also plants containing them (e.g., *Glycyrrhiza glabra*), oleanolic acid and salts thereof, ursolic acid and salts thereof, boswellic acid and salts thereof, betulinic acid and salts thereof, an extract of *Paeonia suffruticosa* and/or *lactiflora*, an extract of *Laminaria saccharina*, extracts of *Centella asiatica*, Canola oil, bisabolol, the phosphoric diester of vitamin E and C, for instance Sepivital EPC® from SEPPIC, camomile extracts, allantoin, omega-3 unsaturated oils such as musk rose oil, blackcurrant oil, Ecchium oil, fish oil or beauty-leaf oil, plankton extracts, capryloyl glycine, a mixture of water lily blossom extract and of palmitoylproline, such as the product marketed under the trademark Seppicalm VG® by SEPPIC, an extract of *Boswellia serrata*, an extract of *Centipeda cunninghami*, such as the product marketed under the trademark Cehami PF® by TRI-K Industries, an extract of sunflower seeds, in particular Helioxine® from Silab, an extract of *Linum usitatissimum* seeds, for instance Sensiline® from Silab, tocotrienols, piperonal, an extract of *Epilobium angustifolium*, such as the product marketed under the trademark Canadian Willowherb Extract by Fytokem Products, Aloe vera, phytosterols, cornflower water, rose water, an extract of mint, in particular of mint leaves, for instance Calmiskin® from Silab, aniseed derivatives, filamentous bacteria, for instance *Vitreoscilla filiformis* as described in EP-761,204 and marketed by Chimex under the trademark Mexoryl SBG®, an extract of rose petals, for instance Rose Flower Herbasol® extract from the company Cosmetochem, shea butter, a mixture of the waxy fraction of barley seeds obtained by supercritical $CO_2$, of shea butter and of argan oil, for instance Stimu-tex AS® from Pentapharm, alkaline-earth metal salts, especially of strontium, a fermented extract of Alteromonas marketed under the trademark Abyssine® by Atrium Biotechnologies; spring water from the Vichy basin, such as waters originating from the Célestin, Chomel, Grande-Grille, Hôpital, Lucas and Parc sources, and preferably water from the Lucas source; an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

Preferred calmatives according to the invention include β-glycyrrhetinic acid and salts or derivatives thereof (stearyl glycyrrhetate, 3-stearoyloxyglycyrrhetic acid or glycyrrhetinic acid monoglucuronide) and also plants containing them (e.g., *Glycyrrhiza glabra*); ursolic acid and salts thereof; extracts of *Centella asiatica*, Canola oil, bisabolol; camomile extracts, allantoin; a mixture of extract of water lily blossom and of palmitoylproline, such as the product marketed under the trademark Seppicalm VG® by SEPPIC; Aloe vera, rose water, extract of mint, in particular of mint leaves, such as Calmiskin® from Silab, filamentous bacteria such as *Vitreoscilla filiformis* as described in EP-761,204 and marketed by Chimex under the trademark Mexoryl SBG®, an extract of rose petals such as Rose Flower Herbasol® extract from the company Cosmetochem, shea butter, a fermented extract of Alteromonas marketed under the trademark Abyssine® by Atrium Biotechnologies; spring water from the Vichy basin, such as waters originating from the Célestin, Chomel, Grande-Grille, Hôpital, Lucas and Parc sources, and preferably water from the Lucas source; an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

Sebo-Regulating or Anti-Seborrhoeic Agents:

The term "sebo-regulating or anti-seborrhoeic agents" especially means agents capable of regulating the activity of the sebaceous glands.

Especially exemplary are:

retinoic acid, benzoyl peroxide, sulfur, vitamin B6 (or pyridoxine), selenium chloride and sea fennel;

mixtures of extract of cinnamon, of tea and of octanoylglycine such as Sepicontrol A5 TEA® from SEPPIC;

the mixture of cinnamon, sarcosine and octanoylglycine marketed especially by SEPPIC under the trademark Sepicontrol A5®;

zinc salts such as zinc gluconate, zinc pyrrolidonecarboxylate (or zinc pidolate), zinc lactate, zinc aspartate, zinc carboxylate, zinc salicylate and zinc cysteate; copper derivatives and in particular copper pidolate such as Cuivridone® from Solabia;

extracts of plants of the species *Arnica montana, Cinchona succirubra, Eugenia caryophyllata, Humulus lupulus, Hypericum perforatum, Mentha piperita, Rosmarinus officinalis, Salvia oficinalis* and *Thymus vulgaris*, all marketed, for example, by Maruzen;

extracts of meadowsweet (*Spiraea ulmaria*), such as the product marketed under the trademark Sebonormine® by Silab;

extracts of the alga *Laminaria saccharine*, such as the product marketed under the trademark Phlorogine® by Biotechmarine;

mixtures of extracts of salad burnet root (*Sanguisorba officinalis/Poterium officinale*), of ginger rhizomes (*Zingiber officinalis*) and of cinnamon bark (*Cinnamomum cassia*), such as the product marketed under the trademark Sebustop® by Solabia;

linseed extracts, such as the product marketed under the trademark Linumine® by Lucas Meyer;

Phellodendron extracts, such as those marketed under the trademark Phellodendron extract BG by Maruzen or Oubaku liquid B by Ichimaru Pharcos;

mixtures of argan oil, of *Serenoa serrulata* (saw palmetto) extract and of sesame seed extract, such as the product marketed under the trademark Regu SEB® by Pentapharm;

mixtures of extracts of willowherb, of *Terminalia chebula*, of nasturtium and of bioavailable zinc (microalgae), such as the product marketed under the trademark Seborilys® by Green Tech;

extracts of *Pygeum afrianum*, such as the product marketed under the trademark *Pygeum afrianum* sterolic lipid extract by Euromed;

extracts of *Serenoa serrulata*, such as the products marketed under the trademark Viapure Sabal by Actives International or those marketed by Euromed;

mixtures of extracts of plantain, of *Berberis aquifolium* and of sodium salicylate, such as the product marketed under the trademark Seboclear® by Rahn;

clove extract, such as the product marketed under the trademark Clove extract powder by Maruzen;

argan oil, such as the product marketed under the trademark Lipofructyl® by Laboratoires Sérobiologiques;

lactic protein filtrates, such as the product marketed under the trademark Normaseb® by Sederma;

extracts of the alga *Laminaria*, such as the product marketed under the trademark Laminarghane® by Biotechmarine;

oligosaccharides of the alga *Laminaria digitata*, such as the product marketed under the trademark Phycosaccharide AC by Codif;

sugar cane extracts, such as the product marketed under the trademark Policosonol® by Sabinsa;

sulfonated shale oil, such as the product marketed under the trademark Ichthyol Pale® by Ichthyol;

European meadowsweet (*Spiraea ulmaria*) extracts, such as the product marketed under the trademark Cytobiol® Ulmaire by Libiol;

sebacic acid, especially marketed in the form of a sodium polyacrylate gel under the trademark Sebosoft® by Sederma;

glucomannans extracted from konjac tuber and modified with alkylsulfonate chains, such as the product marketed under the trademark Biopol Beta by Arch Chemical;

extracts of *Sophora angustifolia*, such as those marketed under the trademark Sophora powder or Sophora extract by Bioland;

extracts of *Cinchona succirubra* bark, such as the product marketed under the trademark Red Bark HS by Alban Muller;

extracts of *Quillaja saponaria*, such as the product marketed under the trademark Panama wood HS by Alban Muller;

glycine grafted onto an undecylenic chain, such as the product marketed under the trademark Lipacide UG OR by SEPPIC;

the mixture of oleanolic acid and of nordihydroguaiaretic acid, such as the product marketed in the form of a gel under the trademark AC.Net by Sederma;

phthalimidoperoxyhexanoic acid;

tri($C_{12}$-$C_{13}$)alkyl citrate marketed under the trademark Cosmacol® ECI by Sasol; tri($C_{14}$-$C_{15}$)alkyl citrate marketed under the trademark Cosmacol® ECL by Sasol;

10-hydroxydecanoic acid, and especially mixtures of 10-hydroxydecanoic acid, of sebacic acid and of 1,10-decanediol, such as the product marketed under the trademark Acnacidol® BG by Vincience; and mixtures thereof.

Preferred anti-seborrhoeic active agents include:

benzoyl peroxide and vitamin B6 (or pyridoxine), zinc salts such as zinc gluconate, zinc pyrrolidonecarboxylate (or zinc pidolate), zinc lactate, zinc aspartate, zinc carboxylate, zinc salicylate and zinc cysteate;

meadowsweet (*Spiraea ulmaria*) extracts, such as the product marketed under the trademark Sebonormine® by Silab;

extracts of the alga *Laminaria saccharina*, such as the product marketed under the trademark Phlorogine® by Biotechmarine;

mixtures of extracts of salad burnet root (*Sanguisorba officinalis/Poterium officinale*), of ginger rhizomes (*Zingiber officinalis*) and of cinnamon bark (*Cinnamomum cassia*), such as the product marketed under the trademark Sebustop® by Solabia;

clove extract, such as the product marketed under the trademark Clove extract powder by Maruzen;

lactic protein filtrates, such as the product marketed under the trademark Normaseb® by Sederma;

European meadowsweet (*Spiraea ulmaria*) extracts, such as the product marketed under the trademark Cytobiol® Ulmaire by Libiol;

sebacic acid, especially marketed in the form of a sodium polyacrylate gel under the trademark Sebosoft® by Sederma;

glycine grafted onto an undecylenic chain, such as the product marketed under the trademark Lipacide UG OR by SEPPIC;

tri($C_{12}$-$C_{13}$)alkyl citrate marketed under the trademark Cosmacol® ECI by Sasol; tri($C_{14}$-$C_{15}$)alkyl citrate marketed under the trademark Cosmacol® ECL by Sasol;

10-hydroxydecanoic acid, and especially mixtures of 10-hydroxydecanoic acid, of sebacic acid and of 1,10-decanediol, such as the product marketed under the trademark Acnacidol® BG by Vincience; and mixtures thereof.

Preferentially, the anti-seborrhoeic active agent is selected from among:

zinc salts such as zinc gluconate, zinc pyrrolidonecarboxylate (or zinc pidolate), zinc lactate, zinc aspartate, zinc carboxylate, zinc salicylate and zinc cysteate; and preferably zinc pyrrolidonecarboxylate (or zinc pidolate) or zinc salicylate;

clove extract, such as the product marketed under the trademark Clove extract powder by Maruzen;

glycine grafted onto an undecylenic chain, such as the product marketed under the trademark Lipacide UG OR by SEPPIC;

tri($C_{12}$-$C_{13}$)alkyl citrate marketed under the trademark Cosmacol® ECI by Sasol; tri($C_{14}$-$C_{15}$)alkyl citrate marketed under the trademark Cosmacol® ECL by Sasol;

and mixtures thereof.

The anti-seborrhoeic active agent is, for example, present in a content ranging from 0.1% to 10% by weight, preferably from 0.1% to 5% by weight and preferentially from 0.5% to 3% by weight relative to the total weight of the composition.

Astringents:

According to the invention, the term "astringents" means agents for combating the dilation of the sebaceous follicles.

As astringents that may be included in the composition according to the invention, exemplary are extracts of mushroom pulp (*Polyporus officinalis*), for instance Laricyl LS8865® from Cognis, extracts of *Terminalia catappa* and *Sambucus nigra*, for instance Phytofirm LS9120® from Cognis, extracts of gall nut, for instance Tanlex VE® from Ichimaru Pharcos, aluminum hydroxychloride, centella extracts (e.g., Plantactiv centella from Cognis), dicetyl dimethylammonium chloride, for instance Varisoft 432 CG® from Degussa, common horse chestnut extracts, mallow extracts, witch-hazel extracts, sweet almond extracts, marshmallow root extracts and linseed extracts, for instance Almondermin LS 3380® from Cognis, burdock extracts, nettle extracts, birch extracts, horsetail extracts, camomile extracts, for instance those marketed under the trademark Extrapone 9 Special® by Symrise, skullcap extracts, European meadowsweet extracts (for example Cytobiol Ulmaire from Libiol), a mixture of extracts of white ginger, of horsetail, of nettle, of rosemary and of yucca, for instance Herb extract B1348® from Bell Flavors & Fragrances, extracts of acacia, of elm, of white willow, of cinnamon, of birch and of meadowsweet, Panama sapogenins, zinc phenolsulfonate from Interchemical, extracts of gentian, of cucumber and of walnut, the mixture of extracts of Ratanhia, of grapefruit, of gumweed and of oak gall, for instance Epilami® from Alban Muller.

Preferred astringents according to the invention include skullcap extracts, European meadowsweet extracts, meadowsweet extracts, gentian extracts and burdock extracts, and mixtures thereof.

Cicatrizing Agents:

Examples of cicatrizing agents that may be included are:

allantoin, urea, certain amino acids, for instance hydroxyproline, arginine, and serine, and also extracts of white lily (for instance Phytéléne Lys 37EG 16295 from Indena), a yeast extract, for instance the cicatrizing agent LS LO/7225B from Laboratoires Sérobiologiques), tamanu oil, extract of *Saccharomyces cerevisiae*, for instance Biodynes® TRF® from Arch Chemical, oat extracts, chitosan and derivatives, for instance chitosan glutamate, carrot extracts, artemia extract, for instance GP4G® from Vincience, sodium acexamate, lavandin extracts, propolis extracts, ximeninic acid and salts thereof, rose hip oil, marigold extracts, for instance Souci Ami® Liposoluble from Alban Muller, horsetail extracts, lemon peel extracts, for instance Herbasol® citron from Cosmetochem, *helichrysum* extracts, common yarrow extracts and folic acid.

Preferred cicatrizing agents according to the invention include arginine, serine, folic acid, tamanu oil, sodium acexamate, horsetail extracts and *helichrysum* extracts, and mixtures thereof.

Anti-Inflammatory Agents:

Particular anti-inflammatory agents according to the invention include cortisone, hydrocortisone, indomethacin, betamethasone, azelaic acid, acetaminophen, diclofenac, clobetasol propionate, folic acid; an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

Preferred anti-inflammatory agents include azelaic acid, folic acid, an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

Antiacne Agents:

In one advantageous aspect of the invention, the composition may also comprise at least one anti-acne active agent.

The term "antiacne active agent" especially means any active agent that has effects on the specific flora of greasy skin, for instance *Propionibacterium acnes* (*P. acnes*). These effects may be bactericidal.

Antibactericidal active agents that may be included are:

active agents and preservatives with anti-microbial activity mentioned in DE-103,24,567, which is incorporated by reference herein, Asiatic acid, the monoethanolamine salt of 1-hydroxy-4-methyl 6-trimethylpentyl-2-pyridone (INCI name: piroctone olamine), marketed especially under the trademark Octopirox® by Clariant;

citronellic acid, perillic acid (or 4-isopropenylcyclohex-1-enecarboxylic acid), glyceryl 2-ethylhexyl ether (INCI name: ethylhexylglycerine), for example marketed under the trademark Sensiva SC50® by Shulke & Mayr, glyceryl caprylate/caprate, for example marketed under the trademark Capmul MCM® by Abitec;

sodium calcium phosphosilicate, especially marketed under the trademarks Bioactive Glasspowder® and Actysse Premier BG® by Schott Glass;

silver-based particles, for example those marketed under the trademark Metashine ME 2025 PS® by Nippon Sheet Glass;

hop cone extract (*Humulus lupulus*) obtained by supercritical $CO_2$ extraction, such as the product marketed under the trademark HOP CO2-TO Extract® by Flavex Naturextrakte, St.-John's Wort extract obtained by supercritical $CO_2$ extraction, such as the product marketed under the trademark St.-John's Wort CO2-TO Extract® by Flavex Naturextrakte, the mixture of extracts of roots of *Scutellaria baicalensis*, of *Paeonia suffruticosa* and *Glycyrrhiza glabra*, such as the product marketed under the trademark BMB-CF® by Naturogin, argan tree extract, for instance Argapure LS9710® from Cognis;

bearberry leaf extracts, for instance the product marketed under the trademark Melfade-J by Pentapharm;

10-hydroxy-2-decanoic acid such as Acnacidol P® from Vincience, sodium ursolate, azelaic acid, diiodomethyl p-tolyl sulfone such as Amical Flowable® from Angus, malachite powder, zinc oxide such as Zincare® from Elementis GMBH, octadecenedioic acid such as Arlatone dioic DCA® from Uniqema; ellagic acid; 2,4,4'-trichloro-2'-hydroxydiphenyl ether (or triclosan), 1-(3',4'-dichlorophenyl)-3-(4'-chlorophenyl)urea (or triclocarban), 3,4,4'-trichlorocarbanilide, 3',4',5'-trichlorosalicylanilide, phenoxyethanol, phenoxypropanol, phenoxyisopropanol, hexamidine isethionate, metronidazole and salts thereof, miconazole and salts thereof, itraconazole, terconazole, econazole, ketoconazole, saperconazole, fluconazole, clotrimazole, butoconazole, oxiconazole, sulfaconazole, sulconazole, terbinafine, ciclopirox, ciclopiroxolamine, undecylenic acid and salts thereof, benzoyl peroxide, 3-hydroxybenzoic acid, 4-hydroxybenzoic acid, phytic acid, N-acetyl-L-cysteine, lipoic acid, azelaic acid and salts thereof, arachidonic acid, resorcinol, 3,4,4'-trichlorocarbanalide, octoxyglycerine or octoglycerine, octanoylglycine such as Lipacid C8G® from SEPPIC, caprylyl glycol, 10-hydroxy-2-decanoic acid, dichlorophenylimidazoldioxolane and derivatives thereof described in WO 93/18743, iodopropynyl butylcarbamate, 3,7,11-trimethyldodeca-2,5,10-trienol or farnesol, phytosphingosines; quaternary ammonium salts, for instance cetyltrimethylammonium salts and cetylpyridinium salts, and mixtures thereof.

Also exemplary are certain surfactants with an anti-microbial effect, for instance sodium cocoamphoacetate or disodium diacetate such as Miranol C2M Conc. NP, betaines, for instance the cocoyl betaine Genagen KB from Clariant, sodium lauryl ether sulfate, for instance Emal 270 D from Kao, decyl glucoside, for instance Plantacare 2000 UP, branched $C_{12-13}$ dialkyl malates, for instance Cosmacol EMI, propylene glycol monoesters, for instance propylene glycol monolaurate, monocaprylate or monocaprate, lauryldimethylamine betaine, for instance Empigen BB/LS, and also polyquaternary ammoniums such as Quaternium-24 or Bardac 2050 from Lonza and those described in FR-0,108,283, and mixtures thereof.

Preferred anti-microbial agents include caprylyl glycol, octoglycerine or octoxyglycerine, and 10-hydroxy-2-decanoic acid, and mixtures thereof.

Other additional anti-acne active agents may be added to the abovementioned anti-acne active agents.

Especially exemplary are active agents with bacterial anti-adhesion effects or agents that act on the biofilm of bacteria to prevent them from multiplying.

Agents for preventing and/or reducing the adhesion of microorganisms include phytanetriol and derivatives thereof as described in EP-1,529,523, plant oils such as wheat germ oil, calendula oil, castor oil, olive oil, avocado oil, sweet almond oil, groundnut oil, jojoba oil, sesame seed oil, apricot kernel oil, sunflower oil and macadamia oil, described in EP-1,133,979, or certain surfactants such as disodium cocoamphodiacetate, oxyethylenated (7 EO) glyceryl cocoate, 18-hexadecenyl succinate, octoxyglyceryl palmitate, octoxyglyceryl behenate, dioctyl adipate, PPG-15 stearyl ether, and the branched $C_{12}$-$C_{13}$ dialkyl tartrates described in EP-1,129,694, and mixtures thereof.

In particular with regard to the propagation of *P. acnes*, or as active agents that act on the biofilm of bacteria to prevent them from proliferating, exemplary are pentylene glycol, Nylon-66 (polyamide 66 fibers), rice bran oil, polyvinyl alcohol such as Celvol 540 PV Alcohol® from Celanese Chemical, rapeseed oil such as Akorex L® from Karlshamns, and fructose derivatives, and mixtures thereof.

The anti-acne active agent may be present in a content ranging from 0.01% to 10% by weight and preferably from 0.05% to 5% by weight relative to the total weight of the composition.

As a function of the nature and/or solubility of the abovementioned active agents, one skilled in this art will know how to select the most suitable embodiment according to the invention.

Exemplary lipophilic active agents that may be included in a kit or in at least one of the compositions of the invention especially include D-α-tocopherol, DL-α-tocopherol, D-α-tocopheryl acetate, DL-α-tocopheryl acetate, ascorbyl palmitate, vitamin F glycerides, D vitamins, vitamin D2, vitamin D3, retinol, retinol esters, retinyl palmitate, retinyl propionate, carotenes including β-carotene, D-panthenol, farnesol, farnesyl acetate, salicylic acid and derivatives thereof, for instance 5-n-octanoylsalicylic acid, α-hydroxy acid alkyl esters such as citric acid, lactic acid, glycolic acid, asiatic acid, madecassic acid, asiaticoside, the total extract of *Centella asiatica*, β-glycyrrhetinic acid, α-bisabolol, ceramides, for instance 2-oleoylamino-1,3-octadecane, phytanetriol, phospholipids of marine origin rich in polyunsaturated essential fatty acids, ethoxyquine, rosemary extract, balm extract, quercetin, extract of dried microalgae, essential oil of bergamot, octyl methoxycinnamate, butylmethoxydibenzoylmethane, octyl triazone, 3,5-di-tert-butyl-4-hydroxy-3-benzylidenecamphor, antibiotics, anti-fungal agents, anaesthetics, analgesics, antiseptics, anti-viral agents, pesticides and herbicides, and mixtures thereof.

The cosmetic and/or dermatological active agents will be present in a kit or in one of the compositions according to the invention in a content ranging from 0.001% to 20% relative to the total weight of the composition, preferably from 0.01% to 10%, even more preferentially from 0.5% to 5% to more preferably from 0.1% to 1% by weight relative to the total weight of the composition.

For "scrubbing" applications, the contents of cosmetic and/or dermatological active agents may range from 1% to 50% by weight relative to the total weight of the composition and preferably from 1% to 30% by weight relative to the total weight of the composition.

Scrubbing is a well-known means for improving the appearance and/or texture of the skin and/or the scalp, especially for improving the radiance and homogeneity of the complexion and/or for reducing the visible and/or tactile irregularities of the skin, and in particular for improving the surface appearance of the skin, for attenuating actinic lentigo, acne or chicken pox marks, and also for preventing, attenuating or combating the signs of aging of the skin, and especially for smoothing out irregularities in the texture of the skin, such as wrinkles and fine lines.

It has the effect of removing a surface part of the skin to be treated (epidermis and possibly the upper layer of the dermis), via chemical methods.

Other Additional Ingredients:

To complement and/or optimize the effects imparted by the cosmetic and/or dermatological active agents mentioned above on the keratin materials, it may be advantageous to incorporate into the compositions of the invention other additional ingredients.

In particular, these additional ingredients may impart an immediate visual effect that will be relayed by the biological effect of the active agents mentioned above. They may also, via a mechanical action (e.g., abrasive fillers), amplify the effect of the biological active agents mentioned above.

Thus, the compositions according to the invention may also comprise at least one agent selected from among matting agents, fillers with a soft-focus effect, fluorescers, agents for promoting the naturally pinkish coloration of the skin, abrasive fillers or exfoliants, and mixtures thereof.

Matting Agents:

The term "matting agent" means agents intended to make the skin visibly more matt and less shiny.

The matting effect of the agent and/or composition containing it may especially be evaluated using a gonioreflectometer, by measuring the ratio R from the specular reflection and the scattered reflection. A value of R of less than or equal to 2 generally reflects a matting effect.

The matting agent may especially be selected from among a rice starch or a corn starch, kaolinite, talc, a pumpkin seed extract, cellulose microbeads, plant fibers, synthetic fibers, in particular polyamide fibers, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof.

Examples of matting agents that may especially be mentioned include:

rice or corn starch, in particular an aluminum starch octenyl succinate marketed under the trademark Dry Flo® by National Starch;

kaolinite;

silicas;

talc;

a pumpkin seed extract as marketed under the trademark Curbilene® by Indena;

cellulose microbeads as described in EP-1,562,562;

fibers, such as silk fiber, cotton fiber, wool fiber, flax fiber, cellulose fiber extracted especially from wood, from vegetables or from algae, polyamide fiber (Nylon®), modified cellulose fiber, poly-p-phenyleneterephthamide fiber, acrylic fiber, polyolefin fiber, glass fiber, silica fiber, aramid fiber, carbon fiber, Teflon® fiber, insoluble collagen fiber, polyester fiber, polyvinyl chloride or polyvinylidene chloride fiber, polyvinyl alcohol fiber, polyacrylonitrile fiber, chitosan fiber, polyurethane fiber, polyethylene phthalate fiber, fibers formed from a mixture of polymers, resorbable synthetic fibers, and mixtures thereof described in EP-1,151,742;

expanded acrylic copolymer microspheres such as those marketed by EXPANCEL under the trademark Expancel 551®;

fillers with an optical effect as described in FR-2,869,796, in particular:

polyamide powders (Nylon®), for instance Nylon 12 particles of the Orgasol type from Arkema, with a mean size of 10 microns and a refractive index of 1.54, silica powders, for instance Silica beads SB150 from Miyoshi with a mean size of 5 microns and a refractive index of 1.45, polytetrafluoroethylene powders, for instance PTFE Ceridust 9205F from Clariant, with a mean size of 8 microns and a refractive index of 1.36, silicone resin powders, for instance the silicone resin Tospearl 145A from GE Silicone with a mean size of 4.5 microns and a refractive index of 1.41, acrylic copolymer powders, especially of polymethyl (meth)acrylate, for instance the PMMA particles Jurymer MBI from Nihon Junyoki, with a mean size of 8 microns and a refractive index of 1.49, or the Micropearl M100® and F 80 ED® particles from the company Matsumoto Yushi-Seiyaku, wax powders, for instance the paraffin wax particles Microease 114S from Micropowders, with a mean size of 7 microns and a refractive index of 1.54, polyethylene powders, especially comprising at least one ethylene/acrylic acid copolymer, and in particular consisting of ethylene/acrylic acid copolymers, for instance the particles Flobeads EA 209 from Sumitomo (with a mean size of 10 microns and a refractive index of 1.48), elastomeric crosslinked organopolysiloxane powders coated with silicone resin, especially with silsesquioxane resin, as described, for example, in U.S. Pat. No. 5,538,793. Such elastomeric powders are marketed under the trademarks KSP-100, KSP-101, KSP-102, KSP-103, KSP-104 and KSP-105 by Shin-Etsu, and talc/titanium dioxide/alumina/silica composite powders such as those marketed under the trademark Coverleaf® AR-80 by Catalyst & Chemicals, mixtures thereof, compounds that absorb and/or adsorb sebum as described in FR-2,869,796. Mention may be made especially of:

silica powders, for instance the porous silica microspheres marketed under the trademark Silica Beads SB-700 marketed by Miyoshi, the products Sunsphere® H51, Sunsphere® H33 and Sunsphere® H53 marketed by Asahi Glass; the polydimethylsiloxane-coated amorphous silica microspheres marketed under the trademark SA Sunsphere® H-33 and SA Sunsphere® H-53 marketed by Asahi Glass;

amorphous mixed silicate powders, especially of aluminum and magnesium, for instance the product marketed under the trademark Neusilin UFL2 by Sumitomo;

polyamide (Nylon®) powders, for instance Orgasol® 4000 marketed by Arkema, and acrylic polymer powders, especially of polymethyl methacrylate, for instance Covabead® LH85 marketed by Wacker; of polymethyl methacrylate/ethylene glycol dimethacrylate, for instance Dow Corning 5640 Microsponge® Skin Oil Adsorber marketed by Dow Corning, or Ganzpearl® GMP-0820 marketed by Ganz Chemical; of polyallyl methacrylate/ethylene glycol dimethacrylate, for instance Poly-Pore® L200 or Poly-Pore® E200 marketed by Amcol; of ethylene glycol dimethacrylate/lauryl methacrylate copolymer, for instance Polytrap® 6603 marketed by Dow Corning;

silicate particles, such as alumina silicate;

mixed silicate particles, such as:

magnesium aluminum silicate particles, such as saponite or hydrated magnesium aluminum silicate with a sodium sulfate marketed under the trademark Sumectone® by Kunimine;

the magnesium silicate, hydroxyethylcellulose, black cumin oil, marrow oil and phospholipids complex or Matipure® from Lucas Meyer, and mixtures thereof.

Preferred matting agents according to the invention include a pumpkin seed extract, a rice or corn starch, kaolinite, silicas, talc, polyamide powders, polyethylene powders, acrylic copolymer powders, expanded acrylic copolymer microspheres, silicone resin microbeads and mixed silicate particles, and mixtures thereof.

Fillers with a Soft-Focus Effect:

These fillers may be any material capable of modifying and hiding wrinkles by virtue of their intrinsic physical properties. These fillers may especially modify wrinkles via a tensioning effect, a covering effect or a soft-focus effect.

Examples of such fillers include the following compounds:

porous silica microparticles, for instance the Silica Beads® SB150 and SB700 from Miyoshi with a mean size of 5 µm; the series-H Sunspheres® from Asahi Glass, for instance Sunspheres H33, H51 with respective sizes of 3.5 and 5 µm;

hollow hemispherical silicone resin particles such as NLK 500®, NLK 506® and NLK 510® from Takemoto Oil and Fat, especially described in EP-A-1 579 849;

silicone resin powders, for instance the silicone resin Tospearl® 145A from GE Silicone, with a mean size of 4.5 µm;

acrylic copolymer powders, especially of polymethyl (meth)acrylate, for instance the PMMA particles Jurymer MBI® from Nihon Junyoki, with a mean size of 8 µm, the hollow PMMA spheres marketed under the trademark Covabead® LH85 by Wacker, and vinylidene/acrylonitrile/methylene methacrylate expanded microspheres marketed under the trademark Expancel®;

wax powders, for instance the paraffin wax particles MicroEase® 114S from MicroPowders, with a mean size of 7 µm;

polyethylene powders, especially comprising at least one ethylene/acrylic acid copolymer, and in particular consisting of ethylene/acrylic acid copolymers, for instance the Flobeads® EA 209 particles from Sumitomo, with a mean size of 10 µm;

crosslinked elastomeric organopolysiloxane powders coated with silicone resin and especially with silsesquioxane resin, under the trademarks KSP-100®, KSP-101®, KSP-102®, KSP-103®, KSP-104® and KSP-105® by Shin-Etsu;

talc/titanium dioxide/alumina/silica composite powders, for instance those marketed under the trademark Coverleaf AR-80® by Catalyst & Chemicals;

talc, mica, kaolin, lauryl glycine, starch powders crosslinked with octenyl succinate anhydride, boron nitride, polytetrafluoroethylene powders, precipitated calcium carbonate, magnesium carbonate, magnesium hydrogen carbonate, barium sulfate, hydroxyapatite, calcium silicate, cerium dioxide and glass or ceramic microcapsules;

hydrophilic or hydrophobic, synthetic or unnatural, mineral or organic fillers such as silk fibers, cotton fibers, wool fibers, flax fibers, cellulose fibers extracted especially from wood, vegetables or algae, Polyamides (Nylon®) fibers, modified cellulose fibers, poly-p-terephthamide fibers, acrylic fibers, polyolefin fibers, glass fibers, silica fibers, aramid fibers, carbon fibers, polytetrafluoroethylene (Teflon®) fibers, insoluble collagen fibers, polyester fibers, polyvinyl chloride fibers, polyvinylidene chloride fibers, polyvinyl alcohol fibers, polyacrylonitriles fibers, chitosan fibers, polyurethane fibers, polyethylene phthalate fibers, fibers formed from a mixture of polymers, resorbable synthetic fibers, and mixtures thereof described in EP-1,151,742;

spherical elastomeric crosslinked silicones, for instance Trefil E-505C® or E-506C® from Dow Corning;

abrasive fillers, which, via a mechanical effect, smooth out the skin microrelief, such as abrasive silica, for instance Abrasif SP® from Semanez or nutshell powders (for example of apricot or walnut, from Cosmetochem).

The fillers with an effect on the signs of aging are especially selected from among porous silica microparticles, hollow hemispherical silicones, silicone resin powders, acrylic copolymer powders, polyethylene powders, crosslinked elastomeric organopolysiloxane powders coated with silicone resin, talc/titanium dioxide/alumina/silica composite powders, precipitated calcium carbonate, magnesium carbonate, magnesium hydrogen carbonate, barium sulfate, hydroxyapatite, calcium silicate, cerium dioxide, glass or ceramic microcapsules, and silk fibers or cotton fibers, and mixtures thereof.

The filler may be a soft-focus filler.

The term "soft-focus" filler means a filler which in addition gives the complexion transparency and a hazy effect. Preferably, the soft-focus fillers have a mean particle size of less than or equal to 15 microns. These particles may be in any form and in particular may be spherical or non-spherical. These fillers are more preferably non-spherical.

The soft-focus fillers may be selected from among silica and silicate powders, especially alumina powder, powders of polymethyl methacrylate (PMMA) type, talc, silica/$TiO_2$ or silica/zinc oxide composites, polyethylene powders, starch powders, polyamide powders, styrene/acrylic copolymer powders and silicone elastomers, and mixtures thereof.

Mention may be made in particular of talc with a number-average size of less than or equal to 3 microns, for example talc with a number-average size of 1.8 microns and especially the product marketed under the trademark Talc P3® by Nippon Talc, Nylon® 12 powder, especially the product marketed under the trademark Orgasol 2002 Extra D Nat Cos® by Atochem, silica particles 1% to 2% surface-treated with a mineral wax (INCI name: hydrated silica (and) paraffin) such as the products marketed by Degussa, amorphous silica microspheres, such as the products marketed under the trademark Sunsphere, for example of reference H-53® by Asahi Glass, and silica microbeads such as those marketed under the trademark SB-700® or SB-150® by Miyoshi, this list not being limiting.

The concentration of these fillers with an effect on the signs of aging in the compositions according to the invention may be from 0.1% to 40%, or even from 0.1% to 20% by weight, relative to the total weight of the composition.

Fluorescers:

The term "fluorescer" means a substance which, under the effect of ultraviolet rays and/or visible light, re-emits in the visible region the portion of light that it has absorbed under the same color as that which it naturally reflects. The naturally reflected color is thus reinforced by the re-emitted color and appears extremely bright.

Examples thereof include colored polyamide and/or formaldehyde/benzoguanamine and/or melamine/formaldehyde/sulfonamide resins, from colored aminotriazine/formaldehyde/sulfonamide co-condensates and/or from metallized polyester flakes and/or mixtures thereof. These fluorescent pigments may also be present in the form of aqueous dispersions of fluorescent pigments.

Also exemplary are the pink-colored fluorescent aminotriazine/formaldehyde/sulfonamide co-condensate with a mean particle size of 3-4 microns marketed under the trademark Fiesta Astral Pink FEX-1 and the blue-colored fluorescent aminotriazine/formaldehyde/sulfonamide co-condensate with a mean particle size of 3-4.5 microns marketed under the trademark Fiesta Comet Blue FTX-60 by Swada, or, alternatively, the yellow-colored benzoguanamine/formaldehyde resin covered with formaldehyde/urea resin marketed under the trademark FB-205 Yellow and the red-colored benzoguanamine/formaldehyde resin covered with formaldehyde/urea resin marketed under the trademark FB-400 Orange Red by UK Seung Chemical, and the orange-colored polyamide resin marketed under the trademark Flare 911 Orange 4 by Sterling Industrial Colors.

The fluorescent substances are preferably present in the composition in a content ranging from 0.1% to 20%, preferably from 0.1% to 15% to more preferably from 0.5% to 3% by weight relative to the total weight of the composition.

When the organic fluorescent substances are white, they are also known as optical brighteners.

The optical brightener has the effect of intensifying the radiance and reviving the shades of cosmetic compositions comprising them on application to the skin.

Among the optical brighteners that are exemplary are stilbene derivatives, in particular polystyrylstilbenes and triazinestilbenes, coumarin derivatives, in particular hydroxycoumarins and aminocoumarins, oxazole, benzoxazole, imidazole, triazole and pyrazoline derivatives, pyrene derivatives and porphyrin derivatives, and/or mixtures thereof.

Such compounds are available, for example, under the trademarks Tinopal SOP® and Uvitex OB® from the company Ciba Geigy.

The preferred optical brighteners are sodium 4,4'-bis[(4,6-dianilino-1,3,5-triazin-2-yl)amino]stilbene-2,2'-disulfonate, 2,5-thiophenediylbis(5-tert-butyl-1,3-benzoxazole) and disodium 4,4'-distyrylbiphenylsulfonate, and/or mixtures thereof.

Agents for Promoting the Naturally Pinkish Coloration of the Skin:

Especially exemplary are:

a self-tanning agent, i.e., an agent which, when applied to the skin, especially to the face, can produce a tan effect that is more or less similar in appearance to that which may result from prolonged exposure to the sun (natural tan) or under a UV lamp;

an additional coloring agent, i.e., any compound that has particular affinity for the skin, which allows it to give the skin a lasting, non-covering coloration (i.e., that does not have a tendency to opacify the skin) and that is not removed either with water or using a solvent, and that withstands both rubbing and washing with a solution containing surfactants. Such a lasting coloration is thus distinguished from the superficial and transient coloration provided, for example, by a makeup pigment; and mixtures thereof.

Examples of self-tanning agents include:
dihydroxyacetone (DHA),
erythrulose, and
the combination of a catalytic system formed from:
manganese and/or zinc oxide salts, and
alkali metal and/or alkaline-earth metal hydrogen carbonates.

The self-tanning agents are generally selected from among monocarbonyl or polycarbonyl compounds, for instance isatin, alloxan, ninhydrin, glyceraldehyde, mesotartaric aldehyde, glutaraldehyde, erythrulose, pyrazoline-4,5-dione derivatives as described in FR-2,466,492 and WO 97/35842, dihydroxyacetone (DHA) and 4,4-dihydroxypyrazolin-5-one derivatives as described in EP-903,342. DHA will preferably be used.

The DHA may be used in free and/or encapsulated form, for example in lipid vesicles such as liposomes, especially described in WO 97/25970.

In general, the self-tanning agent is present in an amount ranging from 0.01% to 20% by weight and preferably in an amount of from 0.1% to 10% of the total weight of the composition.

Other dyes that allow modification of the color produced by the self-tanning agent may also be used.

These dyes may be selected from among synthetic or natural direct dyes.

These dyes may be selected, for example, from red or orange dyes of the fluorane type such as those described in FR-2,840,806. Exemplary are the following dyes:

tetrabromofluoresceine or eosin known under the CTFA name: CI-45380 or Red 21;

phloxin B known under the CTFA name: CI-45410 or Red 27;

diiodofluoresceine known under the CTFA name: CI-45425 or Orange 10;

dibromofluoresceine known under the CTFA name: CI-45370 or Orange 5;

the sodium salt of tetrabromofluoresceine known under the CTFA name: CI-45380 (Na salt) or Red 22;

the sodium salt of phloxin B known under the CTFA name: CI-45410 (Na salt) or Red 28;

the sodium salt of diiodofluoresceine known under the CTFA name:

CI-45425 (Na salt) or Orange 11;

erythrosine known under the CTFA name: CI-45430 or Acid Red 51;

phloxin known under the CTFA name: CI-45405 or Acid Red 98.

These dyes may also be selected from among anthraquinones, caramel, carmine, carbon black, azulene blues, methoxalene, trioxalene, guajazulene, chamuzulene, rose Bengal, eosin 10B, cyanosin and daphinin.

These dyes may also be selected from among indole derivatives, for instance the monohydroxyindoles as described in FR-2,651,126 (i.e., 4-, 5-, 6- or 7-hydroxyindole) or the dihydroxyindoles as described in EP-B-0,425,324 (i.e., 5,6-dihydroxyindole, 2-methyl-5,6-dihydroxyindole, 3-methyl-5,6-dihydroxyindole or 2,3-dimethyl-5,6-dihydroxyindole).

Abrasive Fillers or Exfoliants:

Exemplary exfoliants that may be included in rinse-out compositions according to the invention include exfoliants for scrubbing particles of mineral, plant or organic origin. Thus, polyethylene beads or powder, Nylon powder, polyvinyl chloride powder, pumice powder, ground apricot kernel or walnut husk, sawdust, glass beads and alumina, and mixtures thereof, may be used, for example. Also exemplary are Exfogreen® from Solabia (bamboo extract), extracts of strawberry akenes (Strawberry Akenes from Greentech), peach kernel powder, apricot kernel powder, and finally, in the field of plant powders with an abrasive effect, mention may be made of cranberry kernel powder.

Abrasive fillers or exfoliants that are preferred according to the invention include peach kernel powder, apricot kernel powder, cranberry kernel powder, strawberry akene extracts and bamboo extracts.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES OF SYNTHESIS

Example 1

Synthesis of 4-methyl-1,2-dithiolane-4-carboxylic acid (Compound 1)

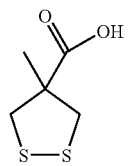

8 g of dichloropivalic acid are placed in a 250 ml three-necked flask on which is mounted a condenser and a dropping funnel. The acid is dissolved in 80 ml of water, slowly adding 4.6 g of $Na_2CO_3$. A solution of 10.7 g of potassium thioacetate is added dropwise and the reaction medium is brought to reflux. 14.9 g of $Na_2CO_3$ are added and the medium is again heated at reflux. After disappearance of the starting material, 7.3 ml of DMSO are added, followed by refluxing. The dithiolane is obtained after acidification by precipitation and drying of the solid under vacuum. A pale yellow solid is obtained.

$^1$H NMR (400 MHz, DMSO-$d_6$): δ ppm 3.69 (d, 2H), 2.95 (d, 2H), 1.53 (s, 3H), ESI−:

[(M, H)−]=163 m/z

Example 2

Synthesis of octyl 4-methyl-1,2-dithiolane-4-carboxylate (Compound 9)

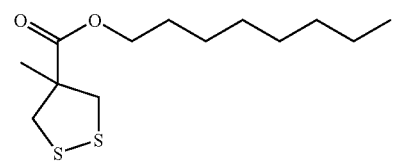 [SMILES: CCCCCCCCOC(=O)C1(C)CSSC1]

1 g of acid (24) and then 0.8 ml of 1-chloro-N,N-2-trimethylpropenylamine (27) are placed in a 100 ml three-necked flask under argon, using a syringe, in 20 ml of dichloromethane. The mixture is stirred for 1 hour and is then added dropwise via a dropping funnel into a reaction medium at −5° C. containing 1.28 ml of triethylamine, 0.96 ml of octanol and 20 ml of dichloromethane. The mixture is stirred. The reaction medium is then washed with water (3×30 ml). The aqueous phase is extracted with 3×10 ml of EtOAc. The combined organic phases are washed with 30 ml of saturated aqueous NaCl solution and then dried over $Na_2SO_4$, filtered and then concentrated under vacuum (500 mbar, T=40° C.) on a rotavapor. The crude product obtained is a yellow oil (m=1.25 g). Purification is performed by flash chromatography on a column of silica (m $SiO_2$=40 g, eluting with a 100/0 and then 98/2 heptane/EtOAc gradient).

After concentrating the fractions on a rotavapor (P=100 mbar, T=40° C.), 1.08 g of pure expected product are obtained.

Yellow oil. Yield=66%; Rf (ester)=0.16 (eluent: cyclohexane);

$^1$H NMR (400 MHz, DMSO-$d_6$): δ ppm 4.08 (t, 2H), 3.57 (d, 2H), 3.02 (d, 2H), 1.58 (m, 2H), 1.40 (s, 3H), 1.29 (m, 10H), 0.86 (t, 3H)

MS m/z (M+, 277; M+23, 299).

The following manipulations were performed under the same conditions described previously, only the nucleophile being changed.

Example 3

Synthesis of S-[2-(acetylamino)ethyl]-4-methyl-1,2-dithiolane-4-carbothioate (Compound 13)

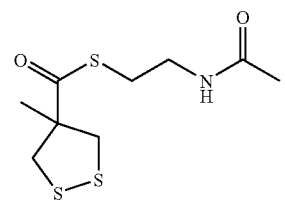

Method identical to that of Example 2: the nucleophile used is N-acetylcysteamine (0.64 ml).

The purification is performed by flash chromatography on a column of silica (m $SiO_2$=40 g, eluting with a 100/0 and then 98/2 DCM/MeOH linear gradient).

After concentrating the fractions on a rotavapor (P=200 mbar, T=40° C.), 0.32 g of a mixture of the expected product with N,N-2-trimethylpropionamide (28) is obtained.

Thick yellow liquid. Yield=10%; Rf (expected product)= 0.3; eluent: 95/5 DCM/MeOH; $^1$H NMR (DMSO-$d_6$): δ ppm 8.03 (t, NH), 3.57 (d, 2H), 3.18 (dt 2H), 3.10 (d, 2H), 2.96 (m, 2H), 1.79 (s, 3H), 1.43 (s, 3H); MS m/z (M+, 266; M+23, 288).

Example 4

Synthesis of N-(2-hydroxyethyl)-4-methyl-1,2-dithiolane-4-carboxamide (Compound 14)

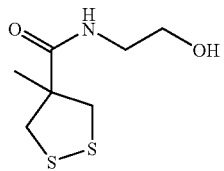

Method identical to that of Example 2: the nucleophile used is ethanolamine (0.36 ml). After filtering the reaction medium, a crude yellow oil is obtained (m=1.850 g).

The purification is performed by flash chromatography on a column of silica (eluting with a 100/0 and then 98/2 DCM/MeOH linear gradient). After concentrating the fractions on a rotavapor (P=500 mbar, T=40° C.), 800 mg of pure expected product are obtained as a yellow oil.

Yield=65%

Rf (expected product)=0.43; eluent: 9/1 DCM/MeOH.

$^1$H NMR (DMSO-$d_6$): δ ppm 7.80 (t, NH), 4.64 (t, OH), 3.53 (d, 2H), 3.40 (dt, 2H), 3.14 (m, 2H), 2.99 (d, 2H), 1.34 (s, 3H); MS m/z (M+, 208; M+23, 230).

Example 5

Synthesis of 4-methyl-1,2-dithiolane-4-carboxamide (Compound 2)

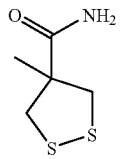

Method (Ex. 5-a) identical to that of Example 2: the nucleophile used is ammonia in isopropanol (9.5 ml). After filtering the reaction medium, a crude yellow oil is obtained (m=1.853 g). The purification is performed by flash chromatography on a column of silica (eluent: DCM). After concentrating the fractions on a rotavapor (P=600 mbar, T=40° C.), 500 mg of pure expected product are obtained as a yellow solid. Yield=52%.

Alternatively, method (Ex. 5-b): to a solution of 1 g of compound 1 in THF with 1.2 equivalents of triethylamine are added, at 0° C., 1.2 equivalents of isobutyl chloroformate. After 2 hours at room temperature, the reaction medium is added to ammonia as a cooled solution, either at 28% in water or at 2N in isopropanol. The medium is stirred at room temperature for the required time and then concentrated under vacuum. The crude product is then taken up in toluene to give, on precipitation, compound 2. Yield=60%

Rf (expected product)=0.45; eluent: 95/5 DCM/MeOH; $^1$H NMR (DMSO-$d_6$): δ ppm 7.38 (s, NH), 7.13 (s, NH), 3.53 (d, 2H), 2.97 (d, 2H), 1.34 (s, 3H); ESI−: [(M, H)−]=162 m/z; ESI+: [(M, Na)+]=186 m/z; ESI+: [(M, H)+]=164 m/z; ESI+: [(M, Na, MeOH)+]=218 m/z Example 6

Synthesis of N-(2,3-dihydroxypropyl)-4-methyl-1,2-dithiolane-4-carboxamide (Compound 15)

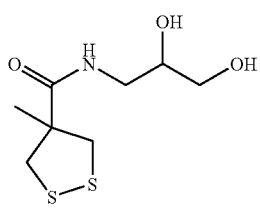

Method identical to that of Example 2: the amount of starting acid used is 0.25 g and the nucleophile used is dimethyldioxalanemethanamine (0.2 ml).

110 mg of pure expected product are obtained as a yellow oil. Yield=26%.

Rf (expected product)=0.51; eluent: 95/5 DCM/MeOH; $^1$H NMR (DMSO-$d_6$): δ ppm 7.77 (t, 1H: NH), 3.55 (dd 4H, H3: diastereoisomers), 3.5 (m, 4H, H7: diastereoisomers), 3.20 (m, 2H, H8: diastereoisomers), 3.05 (dd, 2H: H9 and H9'), 2.99 (dd, 4H, H5), 1.35 (s, 12H, H10+H11: diastereoisomers), 0.9 (d, 3H, H6); MS m/z (M+23, 300).

70 mg of the pure product protected in acetonide form and about 5 g of Dowex resin are placed in a solution of 3 ml of water and 2 ml of THF. The reaction mixture is stirred at room temperature for 20 hours and then at 40° C. for 40 hours.

The reaction medium with the resin is filtered under vacuum and washed with 3×10 ml of water and then 2×10 ml of EtOH. The filtrate is then concentrated on a rotavapor (P=200 mbar, T=40° C.) to give 30 mg of a yellow oil containing two diastereoisomers.

Rf (expected product)=0.24; eluent: 9/1 DCM/MeOH; $^1$H NMR (DMSO-$d_6$): δ ppm 7.80 (t, 1H: NH), 4.73 (d, OH), 4.50 (t, OH), 3.55 (d, 4H), 3.4 (m, 2H), 3.2 (m, 1H), 3.1 (m, 2H), 2.99 (d, 4H), 1.35 (s, 3H); MS m/z (M+, 208; M+23, 230).

Example 7

Synthesis of N-heptyl-4-methyl-1,2-dithiolane-4-carboxamide (Compound 10)

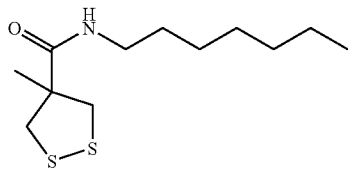 [SMILES: CCCCCCCNC(=O)C1(C)CSSC1]

Method identical to that of Example 2: the nucleophile is 0.22 ml of N-heptylamine.

The crude product obtained is a yellowish oil (m=0.27 g). The purification is performed by flash chromatography on a column of silica (m SiO$_2$=12 g; eluent: 99/1 DCM/MeOH).

After concentrating the fractions on a rotavapor (P=500 mbar, T=40° C.), 0.21 g of pure expected product is obtained as a yellow oil. Yield=54%.

Rf (expected product)=0.5; eluent: 99/1 DCM/MeOH; $^1$H NMR (DMSO-d$_6$): δ ppm 7.78 (t, NH), 3.53 (d, 2H), 3.1 (dt, 2H), 2.97 (d, 2H), 1.41 (tt, 2H), 1.34 (s, 3H), 1.23 (m, 8H), 0.85 (t, 3H); MS m/z (M+, 262; M+23, 284)

Example 8

Synthesis of methyl 2-{[(4-methyl-1,2-dithiolan-4-yl)carbonyl]amino}-4-(methylsulfanyl)butanoate (Compound 12)

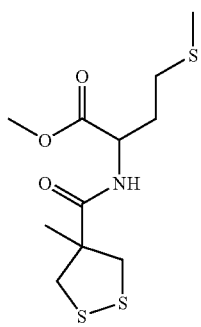

Method identical to that of Example 2: the nucleophile is L-methionine methyl ester.

$^1$H NMR (DMSO-d$_6$): δ ppm 8.13 (d, NH), 4.4 (m, 1H), 3.63 (s, 3H), 3.58 (m, 2H), 3.02 (m, 2H), 2.5 (m, 2H), 2.04 (s, 3H), 1.96 (m, 2H), 1.38 (s, 3H); MS m/z (M+, 310; M+23, 332)

Example 9

Synthesis of N-butyl-4-methyl-1,2-dithiolane-4-carboxamide (Compound 11)

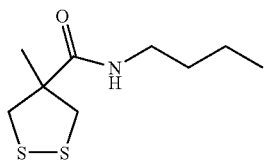

To 1 g of 1,2-dithiolane-4-methyl-4-carboxylic acid in ml of anhydrous THF are added 1.1 equivalents of triethylamine and 1.1 equivalents of diethyl cyanophosphate at 0° C. 1.1 equivalents of n-butylamine are added at 0° C. and the medium is stirred for 1 hour while warming to room temperature. After evaporation and aqueous work-up by extraction, the reconcentrated crude reaction product is purified on a column of silica (eluent: dichloromethane). After evaporating the fractions of interest, a yellow oil is obtained.

$^1$H NMR (DMSO-d$_6$): δ ppm 7.79 (t, NH), 3.53 (d, 2H), 3.1 (dt, 2H), 2.97 (d, 2H), 1.41 (tt, 2H), 1.34 (s, 3H), 1.23 (m, 8H), 0.85 (t, 3H); MS m/z (M+, 262; M+23, 284)

$^1$H NMR (DMSO-d$_6$): δ ppm 7.79 (t, NH), 3.54 (d, 2H), 3.08 (dt, 2H), 2.98 (d, 2H), 1.40 (q, 2H), 1.34 (s, 3H), 1.27 (m, 4H), 0.87 (t, 3H); ESI+: [(M, Na)+]=242 m/z Example 10

Synthesis of ethyl 4-methyl-1,2-dithiolane-4-carboxylate (Compound 4)

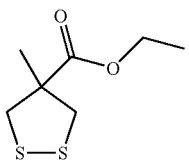

To 1 g of 4-methyl-1,2-dithiolane-4-carboxylic acid in 20 ml of ethanol is added Dowex 50WX8 sulfonic resin (marketed by Aldrich). The mixture is refluxed for 24 hours and then filtered and evaporated to give the pure ethyl ester.

$^1$H NMR (DMSO-d$_6$): δ ppm 4.13 (q, 2H), 3.58 (d, 2H), 3.02 (d, 2H), 1.40 (s, 3H), 1.20 (t, 3H)

ESI+: [(2M, Na)+]=407 m/z

Example 11

Synthesis of N-(4-hydroxy-3-methoxybenzyl)-4-methyl-1,2-dithiolane-4-carboxamide (Compound 16)

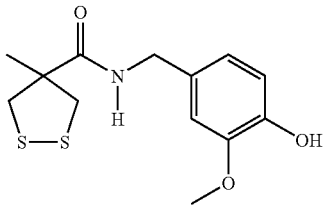 [SMILES: COc1cc(CNC(=O)C2(C)CSSC2)ccc1O]

To 24.3 mmol of dithiolane acid dissolved in 60 ml of dichloromethane, cooled to 0° C. (on an ice bath), are added 24.3 mmol of N-hydroxysuccinimide. The reaction medium is stirred for 30 minutes at 0° C. A solution of 24.3 mmol of DCC in 50 ml of dichloromethane is added and the mixture is then stirred at 20° C. for 4 hours. The reaction medium is filtered and washed, and the filtrate is then evaporated to dryness on a rotavapor at 40° C. under vacuum to give 1-{[(4-methyl-1,2-dithiolan-4-yl)carbonyl]oxy}pyrrolidine-2,5-dione. (m=7 g, quantitative yield). To 1.58 mmol of 1-{[(4-methyl-1,2-dithiolan-4-yl)carbonyl]oxy}pyrrolidine-2,5-dione are added 10 ml of methyl-THF, 3.16 mmol of 4-(aminomethyl)-2-methoxyphenol hydrochloride and 3.16 mmol of triethylamine. After stirring overnight, the mixture is filtered, rinsed with methyl-THF and then evaporated. Flash chromatography, eluting with 98/2 dichloromethane/methanol, gives compound 16 in the form of a yellow oil (yield=84%).

$^1$H NMR (DMSO-d$_6$): δ ppm 1.39 (s, 3H); 3.03 (d, 2H); 3.56 (d, 2H), 3.63 (s, 3H, OCH$_3$), 4.21 (d, 2H), 6.64 (dd, 1H, Ar), 6.69 (d, 1H, Ar), 6.80 (d, 1H, Ar), 8.31 (t, 1H, NH), 8.79 (s, 1H, OH)

ESI+: [(M, H)+]=300 m/z

Example 12

Synthesis of N-[2-(4-hydroxy-3-methoxyphenyl)ethyl]-4-methyl-1,2-dithiolane-4-carboxamide (Compound 17)

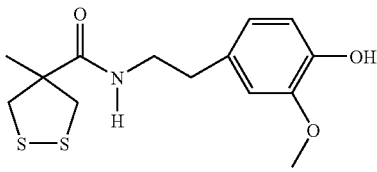

Same method as for compound 16, with 4-(2-aminoethyl)-2-methoxyphenol hydrochloride. Yellow oil. Yield=64%.

$^1$H NMR (DMSO-$d_6$): δ ppm 1.31 (s, 3H); 2.63 (t, 2H), 2.97 (d, 2H); 3.24 (m, 2H, NCH$_2$) 3.53 (d, 2H), 3.75 (s, 3H, OCH$_3$), 6.57 (dd, 1H, Ar), 6.67 (d, 1H, Ar), 6.74 (d, 1H, Ar), 8.86 (t, 1H, NH), 8.67 (s, 1H, OH)

ESI+: [(M, H)+]=314 m/z

Example 13

Synthesis of N,N-diethyl-4-methyl-1,2-dithiolane-4-carboxamide (Compound 18)

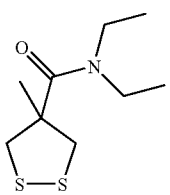

To 2.26 mmol of compound 1 are added 5 ml of anhydrous dichloromethane and 0.1 ml of anhydrous DMF. The mixture is cooled to 0° C., followed by addition of 2.7 mmol of oxalyl chloride. The mixture is stirred at 20° C. and then added, at 0° C., to a mixture of 2.26 mmol of diethylamine, 5 ml of anhydrous dichloromethane and 6.8 mmol of diisopropylethylamine. The reaction medium is stirred for 3 hours at 20° C. When the reaction is complete, the medium is diluted in 50 ml of dichloromethane and then washed with 2×30 ml of water and 1×50 ml of saturated NH$_4$Cl solution, and then dried over Na$_2$SO$_4$ and evaporated to dryness on a rotavapor. After flash chromatography (eluent: heptane/EtOAc), compound 18 is isolated in the form of a yellow oil (yield=48%).

$^1$H NMR (DMSO-$d_6$): δ ppm 1.36 (s, 3H); 3.15 (d, 2H); 3.50 (d, 2H), 3.3 (m, 2×2H), 1.07 (m, 2×3H)

ESI+: [(M, H)+]=220 m/z

Example 14

Synthesis of 4-methyl-N-(1-methylethyl)-1,2-dithiolane-4-carboxamide (Compound 20)

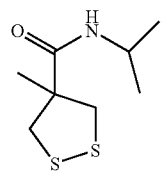

Same method as in Example 19, with isopropylamine. Beige-colored solid. Yield=54%

$^1$H NMR (DMSO-$d_6$): δ ppm 1.06 (d, 2×3H); 1.33 (s, 3H, Hc); 2.99 (d, 2H, Hb); 3.56 (d, 2H, Ha); 3.88 (m, 1H), ESI+: [(M, H)+]=206 m/z

Example 15

Synthesis of 4-methyl-N-phenyl-1,2-dithiolane-4-carboxamide (Compound 21)

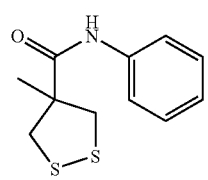

Same method as in Example 19, with aniline. Yellow oil. Yield=70%

$^1$H NMR (DMSO-$d_6$): δ ppm 1.51 (s, 3H, Hc); 2.99 (d, 2H, Hb); 3.75 (d, 2H, Ha), 7.08 (t, 1H, Ar), 7.3 (t, 2H, Ar), 7.60 (d, 2H, Ar), 9.56 (s, 1H, NH)

ESI+: [(M, H)+]=240 m/z

Examples of Formulation 16 to 19

| Compositions | Ex. 16 (*) | Ex. 17 | Ex. 18 | Ex. 19 | Ex. 20 |
|---|---|---|---|---|---|
| C$_{12}$/C$_{15}$ alkyl benzoate | 10.0 | 10.0 | 10.0 | 10.0 | 10.0 |
| Glyceryl monostearate/PEG stearate (100 EO) mixture | 6.5 | 6.5 | 6.5 | 6.5 | 6.5 |
| Polyacrylamide (and) C13-C14 Isoparaffin (and) Laureth-7 | 1.0 | 1.0 | 1.0 | 1.0 | 1.0 |
| Compound 9 of the invention | — | 10.0 | — | — | — |
| Compound 10 of the invention | — | — | 10.0 | — | 10.0 |
| Compound 1 of the invention | — | — | — | 10.0 | — |
| Compound 2 of the invention | — | — | — | 10.0 | — |
| 4-tert-Butyl-4'-methoxydibenzoyl-methane (Parsol 1789) | 1.0 | 1.0 | 1.0 | 1.0 | 1.0 |

| Compositions | Ex. 16 (*) | Ex. 17 | Ex. 18 | Ex. 19 | Ex. 20 |
|---|---|---|---|---|---|
| Glycerol | 5.0 | 5.0 | 5.0 | 5.0 | 5.0 |
| Demineralized water | qs 100 | qs 100 | qs 100 | qs 100 | qs 100 |

(*) outside the invention

Photostabilization of 4-(tert-butyl)-4'-methoxydibenzoylmethane:

Principle of the Method:

The percentage loss of dibenzoylmethane derivative, induced by exposure to a sun simulator, of a formula spread as films about 20 μm thick is measured.

The evaluation is performed by HPLC analysis of the screening agent as a solution, after extraction of the films, by comparing irradiated and non-irradiated samples.

Materials and Conditions Used:

These emulsions are spread out as films about 20 μm thick onto a frosted face of a silica disc. The exact amount is determined by weighing. Three films are exposed to an Oriel 1000 W sun simulator equipped with a 4-inch outlet, with a 81017 filter and a dichroic mirror delivering a dose of 21.6 J/cm² of UV-A (corresponding to 1 hour of exposure to UV-A). Three other films serve as references. The samples are exposed in a horizontal position.

UV-meter: Osram Centra machine equipped with two reading heads, one for UV-A and the other for UV-B. The simulator/UV-meter assembly is calibrated annually by spectroradiometry.

Irradiance measurements are taken at the start and entered of exposure by placing the reading heads in the position of the sample.

The irradiances are: 0.35-0.45 mW/cm² in UV-B and 14-16 mW/cm² in UV-A.

At the end of the exposure, each support disc is placed in a 600 ml jar with 10 ml of a suitable solvent (generally EtOH); the assembly is placed for 5 minutes in an ultrasonication tank.

The solution is then transferred into flasks suited to the support compatible with the HPLC analysis machine used.

The analytical conditions may be adjusted as a function of the active agent tested.

The residual butylmethoxydibenzoylmethane content is measured by chromatography: HPLC chain with a diode array detector (Waters).

The residual butylmethoxydibenzoylmethane (avobenzone) content after irradiation in the same support not containing any dithiolane-based compound of formula (I) (formula I comparative example) is also measured.

The calculation of the residual content (%) is performed from the averages obtained on the samples exposed and not exposed to UV, as described below:

| Compositions | Residual percentage of avobenzone after 1 hour of UV-A exposure |
|---|---|
| Ex. 16 (outside the invention): (dibenzoylmethane alone) | 21.0 ± 1.5 |
| Ex. 17: compound 9 + dibenzoylmethane | 89.5 ± 1.0 |
| Ex. 18: Compound 10 + dibenzoylmethane | 87.5 ± 1.7 |
| Ex. 19: compound 1 + dibenzoylmethane | 83.1 ± 0.9 |
| Ex. 20: compound 2 + dibenzoylmethane | 73.7 ± 1.5 |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/sunscreen composition comprising at least one UV-screening system which comprises:
   (a) at least one dibenzoylmethane compound and a photostabilizing amount of
   (b) at least one dithiolane compound of formula (I) below:

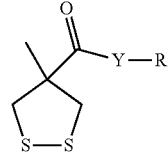

in which:
   Y is O or NR₁;
   R₁ is a hydrogen atom, a saturated linear $C_1$-$C_{20}$ or branched $C_3$-$C_{20}$ or unsaturated $C_2$-$C_{20}$ alkyl hydrocarbon-based radical, an aryl radical optionally substituted with one or more hydroxyl groups and/or with one or more $C_1$-$C_8$ alkoxy radicals;
   R is a hydrogen atom, a saturated linear $C_1$-$C_{20}$ or branched $C_3$-$C_{20}$ or unsaturated $C_2$-$C_{20}$ alkyl hydrocarbon-based radical, an aryl radical or a saturated $C_1$-$C_8$ alkyl radical containing an aryl substituent optionally substituted with one or more hydroxyl groups and/or with one or more $C_1$-$C_8$ alkoxy radicals;
   R optionally bears one or more substituents selected from among $OR_2$, $SR_2$, $NR_2R_3$ and $COOR_2$ in which:
   $R_2$ is a hydrogen atom or a saturated linear $C_1$-$C_5$ or branched $C_3$-$C_5$ or unsaturated $C_2$-$C_5$ hydrocarbon-based radical, or an aryl radical;
   $R_3$ is a hydrogen atom, a saturated linear $C_1$-$C_5$ or branched $C_3$-$C_5$ or unsaturated $C_2$-$C_5$ hydrocarbon-based radical, an aryl radical, or an acetyl radical;
   with the proviso that R and R₁ may together form a ring member selected from among pyrrolidine, pyrroline, piperidine, piperazine, morpholine, thiomorpholine and azepine; and also the salts, chelates, solvates and optical isomers thereof, formulated into a topically applicable, cosmetically/dermatologically acceptable support therefor.

2. The cosmetic/sunscreen composition as defined by claim 1, in which the compound of formula (I) is selected from among those for which Y is $NR_1$ and $R_1$=H.

3. The cosmetic/sunscreen composition as defined by claim 1, in which the compound of formula (I) is selected from among those for which R=H or a $C_1$-$C_8$ alkyl radical.

4. The cosmetic/sunscreen composition as defined by claim 1, in which the compound of formula (I) is selected from among the following compounds:

| No. | Structure | Chemical name |
|---|---|---|
| 1 | 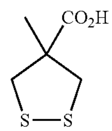 | 4-Methyl-1,2-dithiolane-4-carboxylic acid |
| 2 | 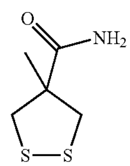 | 4-Methyl-1,2-dithiolane-4-carboxamide |
| 3 | 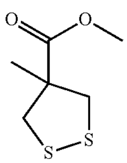 | Methyl 4-methyl-1,2-dithiolane-4-carboxylate |
| 4 | 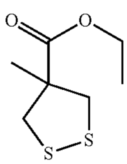 | Ethyl 4-methyl-1,2-dithiolane-4-carboxylate |
| 5 | 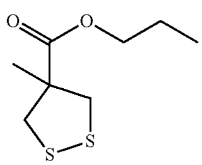 | Propyl 4-methyl-1,2-dithiolane-4-carboxylate |
| 6 | 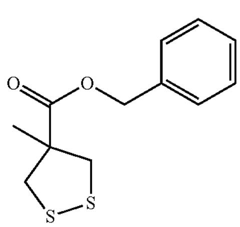 [SMILES: CC1(C(=O)OCc2ccccc2)CSSC1] | Benzyl 4-methyl-1,2-dithiolane-4-carboxylate |
| 7 | 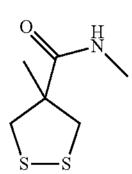 | N-Methyl 4-methyl-1,2-dithiolane-4-carboxamide |
| 8 | | {[(4-Methyl-1,2-dithiolan-4-yl)-carbonyl]-amino}acetic acid |
| 9 | | Octyl 4-methyl-1,2-dithiolane-4-carboxylate |
| 10 | | N-Heptyl-4-methyl-1,2-dithiolane-4-carboxamide |
| 11 | | N-Butyl-4-methyl-1,2-dithiolane-4-carboxamide |
| 12 | | Methyl 2-{[(4-methyl-1,2-dithiolan-4-yl)-carbonyl]-amino}-4-(methyl-sulfanyl)-butanoate |
| 13 | | S-[2-(Acetyl-amino)-ethyl] 4-methyl-1,2-dithiolane-4-carbothioate |
| 14 | | N-(2-Hydroxy-ethyl)-4-methyl-1,2-dithiolane-4-carboxamide |

-continued

| No. | Structure | Chemical name |
|---|---|---|
| 15 | 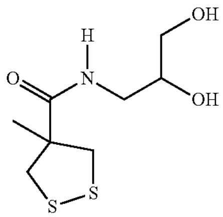 | N-(2,3-Dihydroxy-propyl)-4-methyl-1,2-dithiolane-4-carboxamide |
| 16 | 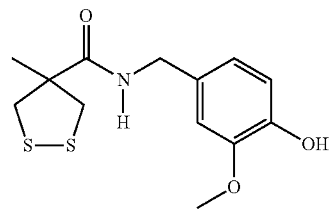 [SMILES: COc1cc(CNC(=O)C2(C)CSSC2)ccc1O] | N-(4-Hydroxy-3-methoxy-benzyl)-4-methyl-1,2-dithiolane-4-carboxamide |
| 17 | 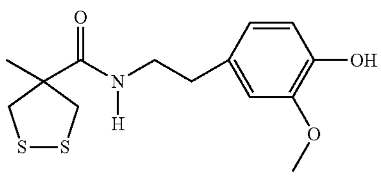 [SMILES: COc1cc(CCNC(=O)C2(C)CSSC2)ccc1O] | N-[2-(4-Hydroxy-3-methoxy-phenyl)-ethyl]-4-methyl-1,2-dithiolane-4-carboxamide |
| 18 | 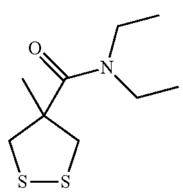 | N,N-Diethyl-4-methyl-1,2-dithiolane-4-carboxamide |
| 19 | 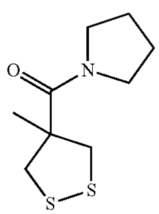 | [(4-Methyl-1,2-dithiolan-4-yl)-carbonyl]-pyrrolidine |
| 20 | 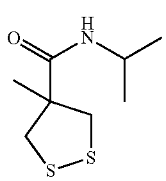 | 4-Methyl-N-(1-methyl-ethyl)-1,2-dithiolane-4-carboxamide |
| 21 | 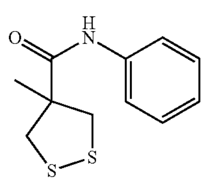 | 4-Methyl-N-phenyl-1,2-dithiolane-4-carboxamide |
| 22 | 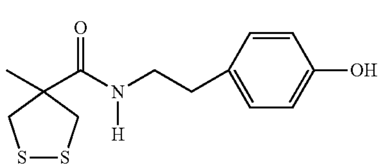 [SMILES: CC1(C(=O)NCCc2ccc(O)cc2)CSSC1] | N-[2-(4-Hydroxy-phenyl)-ethyl]-4-methyl-1,2-dithiolane-4-carboxamide |

-continued

| No. | Structure | Chemical name |
|---|---|---|
| 23 | 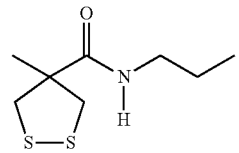 | N-Propyl-4-methyl-1,2-dithiolane-4-carboxamide |
| 24 | 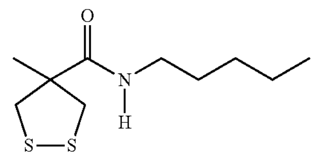 | N-Pentyl-4-methyl-1,2-dithiolane-4-carboxamide |
| 25 | 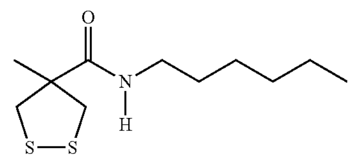 | N-Hexyl-4-methyl-1,2-dithiolane-4-carboxamide. |

5. The cosmetic/sunscreen composition as defined by claim 4, in which the compound of formula (I) is selected from among the following compounds:

| No. | Structure | Chemical name |
|---|---|---|
| 1 | 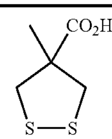 | 4-Methyl-1,2-dithiolane-4-carboxylic acid |
| 2 | 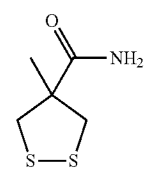 | 4-Methyl-1,2-dithiolane-4-carboxamide |
| 9 | 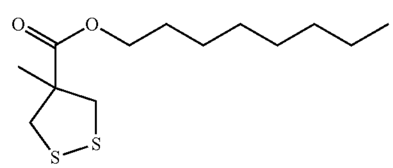 [SMILES: CCCCCCCCOC(=O)C1(C)CSSC1] | Octyl 4-methyl-1,2-dithiolane-4-carboxylate |
| 10 | 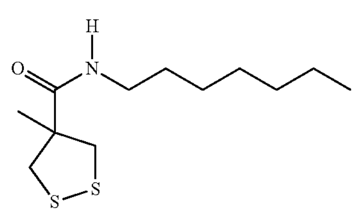 [SMILES: CCCCCCCNC(=O)C1(C)CSSC1] | N-Heptyl-4-methyl-1,2-dithiolane-4-carboxamide. |

6. The cosmetic/sunscreen composition as defined by claim 1, in which the dibenzoylmethane derivative is 4-(tert-butyl)-4'-methoxydibenzoylmethane, or Butyl Methoxy Dibenzoylmethane, of the following formula:

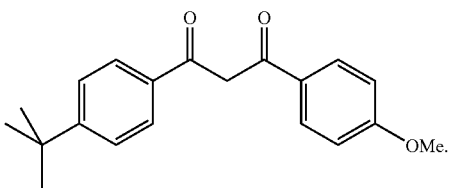 [SMILES: COc1ccc(C(=O)CC(=O)c2ccc(C(C)(C)C)cc2)cc1]

7. The cosmetic/sunscreen composition as defined by claim 1, further comprising other UV-A-active and/or UV-B-active organic or mineral screening agents, which are water-soluble or liposoluble, or insoluble in a cosmetic solvent.

8. The cosmetic/sunscreen composition as defined by claim 7, in which the other organic screening agents are selected from among anthranilates; cinnamic derivatives; salicylic derivatives; camphor derivatives; benzophenone derivatives; β-,β-diphenylacrylate derivatives; triazine derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; α-alkylstyrene-based dimers; 4,4-diarylbutadienes; merocyanin derivatives; and mixtures thereof.

9. The cosmetic/sunscreen composition as defined by claim 8, comprising organic UV-screening agent(s) selected from among the following compounds:

Ethylhexyl methoxycinnamate,
Ethylhexyl salicylate,
Homosalate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Bis(ethylhexyloxyphenol)methoxyphenyltriazine,
Ethylhexyltriazone,
Diethylhexylbutamidotriazone,
2,4bis(4'-aminobenzoate de n-butyle)-6-(aminopropyl-trisiloxane)-s-triazine,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4,6-Tris(biphenyl-4-yl)-1,3,5-triazine,
2,4,6-Tris(terphenyl)-1,3,5-triazine,
Drometrizole trisiloxane,
Polysilicone-15,
1,1-Dicarboxy(2,2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine,
Octyl 5-N,N-diethylamino-2-phenylsulfonyl-2,4-pentadienoate,
and mixtures thereof.

10. The cosmetic/sunscreen composition as defined by claim 7, comprising mineral screening agents that are coated or uncoated metal oxide pigments.

11. The cosmetic/sunscreen composition as defined by claim 10, in which the coated or uncoated metal oxide pigments have a mean primary particle size ranging from 5 nm to 100 nm.

12. The cosmetic/sunscreen composition as defined by claim 10, in which the coated or uncoated metal oxide pigments are selected from the group consisting of titanium oxide, iron oxide, zinc oxide, zirconium oxide and cerium oxide pigments, and mixtures thereof.

13. The cosmetic/sunscreen composition as defined by claim 1, comprising an oil-in-water or water-in-oil emulsion.

14. A process for improving the chemical stability, with respect to UV radiation, of at least one dibenzoylmethane compound, comprising formulating said at least one dibenzoylmethane compound with a thus effective amount of at least one dithiolane compound of formula (I) as defined in claim 1.

15. A process of improving the efficacy of at least one dibenzoylmethane compound with respect to UV-A rays, comprising formulating same with at least one dithiolane compound of formula (I) as defined in claim 1.

16. A regime or regimen for photoprotecting the skin against the damaging effects of UV-radiation, comprising applying thereon a thus effective amount of the cosmetic/sunscreen composition as defined by claim 1.

* * * * *